United States Patent
Dickie et al.

(10) Patent No.: US 9,317,663 B2
(45) Date of Patent: Apr. 19, 2016

(54) METHOD OF USING A MEDICATION REMINDER AND COMPLIANCE SYSTEM INCLUDING AN ELECTRONIC PILL BOX

(71) Applicant: Next Paradigm Inc., Toronto (CA)

(72) Inventors: Robert G. Dickie, King (CA); Norman P. Paul, Toronto (CA)

(73) Assignee: Next Paradigm Inc., Toronto, Ontario (CA)

( * ) Notice: Subject to any disclaimer, the term of this patent is extended or adjusted under 35 U.S.C. 154(b) by 195 days.

(21) Appl. No.: 13/966,037

(22) Filed: Aug. 13, 2013

(65) Prior Publication Data

US 2015/0048100 A1    Feb. 19, 2015

(51) Int. Cl.
| | |
|---|---|
| *G08B 21/00* | (2006.01) |
| *G06F 19/00* | (2011.01) |
| *A61J 7/04* | (2006.01) |
| *A61J 7/00* | (2006.01) |

(52) U.S. Cl.
CPC ........... *G06F 19/3462* (2013.01); *A61J 7/0084* (2013.01); *A61J 7/0481* (2013.01); *A61J 7/0418* (2015.05); *A61J 2007/0418* (2013.01); *A61J 2200/30* (2013.01); *A61J 2205/20* (2013.01)

(58) Field of Classification Search
CPC .................................. A61J 7/04; A61J 7/0409
USPC ................. 340/309.16, 309.7, 573.1; 368/10; 221/0.2; 206/534
See application file for complete search history.

(56) References Cited

U.S. PATENT DOCUMENTS

| | | | |
|---|---|---|---|
| 3,762,601 | A | 10/1973 | McLaughlin |
| 4,275,384 | A | 6/1981 | Hicks et al. |
| 4,382,688 | A | 5/1983 | Machamer |
| 4,748,600 | A | 5/1988 | Urquhart |
| 5,020,037 | A | 5/1991 | Raven |
| 5,099,463 | A | 3/1992 | Lloyd et al. |
| 5,200,891 | A | 4/1993 | Kehr et al. |
| 5,850,937 | A | 12/1998 | Rauche |
| 6,048,087 | A | 4/2000 | Laurent et al. |
| 2003/0080854 | A1 | 5/2003 | Brakus |
| 2005/0075908 | A1 | 4/2005 | Stevens |
| 2010/0314282 | A1 | 12/2010 | Bowers |
| 2012/0006708 | A1* | 1/2012 | Mazur ................... A61J 7/0481 206/438 |

FOREIGN PATENT DOCUMENTS

| | | |
|---|---|---|
| CN | 103315909 | 9/2013 |
| FR | 2892016 | 4/2007 |
| WO | 0217850 | 3/2002 |
| WO | 2012111034 | 8/2012 |
| WO | 2013071225 | 5/2013 |

* cited by examiner

*Primary Examiner* — Jeffrey Hofsass
(74) *Attorney, Agent, or Firm* — Sand & Sebolt

(57) ABSTRACT

A medication reminder and compliance system including a pill box, a pill box and electronic device; or a pill box, electronic device and remote server. The pill box includes several detachable dosettes, each divided into several chambers having a door. A two-color LED is disposed beneath each chamber and is activated when a specific reminder time is reached. The LED initially illuminates the associated chamber with a green light but changes to a flashing red light if the door is not opened within a preset time. A switch engaged with the door deactivates the LED when the door is opened. The electronic device communicates with the pill box and alerts the patient when it is time to take medication. A remote server which communicates with both the pill box and electronic device can be programmed to control the reminder schedule and monitor the patient's compliance with a prescribed medication regimen.

9 Claims, 22 Drawing Sheets

METHOD OF USING A MEDICATION REMINDER AND COMPLIANCE SYSTEM INCLUDING AN ELECTRONIC PILL BOX

BACKGROUND OF THE INVENTION

1. Technical Field

This invention relates generally to pill boxes for storing several different medications. More particularly, this invention relates to an electronic pill box. Specifically, this invention is directed to an electronic pill box that illuminates a specific chamber on the box when a prescheduled reminder time is reached and deactivates the device that illuminates that chamber when the door to the same is opened. An electronic device such as a cell phone as well as a remote server may be utilized as part of the system to remind the patient to take a particular dose and to monitor the patient's compliance with a prescribed medication regimen.

2. Background Information

Doctors prescribe medication for patients suffering from a variety of illnesses. One of the issues that is fairly common is that patients frequently do not follow the exact dosage regimen prescribed by the physician. They will tend to forget to take a dose at a prescribed time or will accidently double up dosages when they can't remember if they took the medication at a prescribed time. Because the prescribed regimen is not being followed, the healing which should occur through action of the medication on their body may be slowed or the patient could actually put their health in jeopardy by overdosing themselves.

There have been attempts in the prior art to develop some type of system to assist a patient in keeping prescribed medication regimens. For example, U.S. Pat. No. 3,762,601 (McLaughlin) discloses a cabinet that has several independent compartments into which individual doses of medication are placed. The cabinet includes some type of timing mechanism which automatically opens a locking mechanism engaged with a door to a particular compartment when a preset time arrives. The locking mechanisms are timed for a 24 hour period and the system includes a main signal light on the side of the cabinet to alert a caregiver that it is time to dispense medicine to the patient. A keyed master door blocks access to individual compartment doors. A light is also associated with each compartment in the cabinet and, if a compartment is unlocked, the associated light will be illuminated to indicate the unlocked condition of the compartment. The downfall with this system is that the master door has to be unlocked by a person other than the patient, such as a nurse. If the nurse does not unlock the master door then there will be no access to the unlocked compartment. If the master door is unlocked and a compartment door is automatically unlocked and opened at the preset time and the patient is not in any condition to access the medicine in the compartment, that medicine could be accessed by other persons, such as children. Additionally, this type of cabinet is not designed to be carried around by the patient. It is configured to be mounted permanently on a wall, for example.

Hicks (U.S. Pat. No. 4,275,384) discloses a portable medicine cabinet with a computerized timer. Predetermined time intervals are entered into the computerized timer. The timer is connected to an indicator mechanism which indicates the predetermined time intervals and which of the medicines should be removed from compartments within the cabinet. Each compartment in the cabinets is cylindrical in shape and has a hinged door positioned to close off access to the compartment. A means for entering time into the computer is provided on the cabinet. The computer generates an output signal when a present time is reached and this signal causes a signal light provided on the exterior surface of the cabinet proximate a compartment to become illuminated so that the patient knows which medicine to take. The cabinet also includes a screen for displaying time and a digital number for the compartment to be accessed; and further includes a buzzer to alert the patient that it is time to take a medicine from the indicated compartment.

U.S. Pat. No. 4,382,688 (Machamer) discloses a portable medical dispenser that includes a door which is retained in a closed position by way of a latch. The system includes a timer and an electronic memory. When a preset time is reached an audible alarm is sounded to notify the user that it is time to take a medication within the dispenser. The alarm may also include a flashing of the time display on the dispenser. A switch is mounted adjacent the door latch to detect when the door is opened. A disarming mechanism is provided and is capable of being programmed to disarm the alarm for a particular period. This is utilized when the portable dispenser is used for retaining birth control pills and no reminders to the user are needed for several days each month. The electronic memory cannot be altered by the user.

Urquhart (U.S. Pat. No. 4,748,600) discloses a dispenser which controls doses of pharmaceuticals to a patient. The dispenser includes a central processing unit which is programmed with an initial dosing regimen and is able to record and monitor dispensing of pharmaceuticals from the dispenser. The dispenser includes, a timer and means for recording the actual times medicines are dispensed and for calculating discrepancies between the prescribed dispensing time and the actual dispensing time. The dispenser further includes a means for calculate a dosing correction factor for the patient based on the information gathered by the dispenser. The dispenser includes a display screen for displaying information it gathers and calculates. The patient is able to input information into the dispenser to be used in the various calculations performed by the dispenser. The dispenser is also equipped to provide a physician with information regarding any deviations in the dosing regimen.

Raven (U.S. Pat. No. 5,020,037) discloses a pill box that includes a timer to track time and an alarm to notify a patient when to take medication retained within the pill box at particular preset times. The alarm is deactivated when a door to a compartment in the pill box is opened. The pill box includes an electronic memory which records each time the alarm is canceled and a display screen capable of displaying the recorded information. The times set in the timer can only be adjusted if the door to a compartment is in the open position.

U.S. Pat. No. 5,099,463 to Lloyd et al discloses a medicine dispenser that includes a timer and a display for indicating the time at which a particular medicine should be taken and for giving the patient visual instructions. The dispenser is configured so that the medication can be kept in the original containers provided by a pharmacist. The dispenser is programmed to queue the medications so that they are able to be taken in the correct sequence. Sensors are provided in the various compartments of the dispenser to verify that medication containers are returned to the dispenser after use. An alarm system is also provided in the dispenser to alert the patient that it is time to take a medicine from one of the compartments. The alarm system generates a sound and/or illuminates a light to alert the patient that action must be taken.

Kehr et al (U.S. Pat. No. 5,200,891) discloses a medication dispenser having a programmable microprocessor and a number of compartments, each of which may store medication. A signaling system is provided to alert the patient to the fact that medication should be taken, to identify which compartment it should be removed from; and the quantity of medication that is to be taken at that time. An alarm will sound if the designated compartment is not opened within a certain period of time. The alarm is disarmed if the compartment door is opened. The dispenser includes a display screen for displaying pertinent information. The device also includes a means for the patient to program the microprocessor.

U.S. Pat. No. 5,850,937 (Rauche) discloses a dispenser that is capable of alerting a patient that it is time to take a medication from one of a plurality of compartments. The dispenser includes a real-time clock for tracking time and a memory for storing times for taking medication. There is also an input for entering the times to be stored in the memory and an alarm system that is activated when the tracked real time corresponds to the stored time for taking medication. The dispenser housing is transparent so that a medication summary sheet retained within a compartment is visible when the compartment is closed. There are mounting devices within the compartments for retaining an inhaler in a particular orientation therein. The door for each compartment is locked into placed by an electronic mechanism and the door can only be moved to an open position when the electronic mechanism is deactivated. The dispenser also includes a real-time clock, a display, a push-button matrix for entering a code sequence, a buzzer, a light, and a vibratory mechanism, the last three components being provided to selectively alert a patient that it is time to take a medication from the dispenser. The dispenser also includes a programmable memory and control means for controlling various components that make up the dispenser.

Finally, U.S. Pat. No. 6,048,087 (Laurent et al) discloses an electronic pill box that includes multiple compartments for retaining doses of medicine therein. The pill box includes a microprocessor that can have prescription data inputted therein. A display is provided on the device and each compartment has a pill dispenser that is adapted to dispense pharmaceuticals of various forms and sizes therefrom. An automatic controller associated with each compartment controls medication movement from the compartment. Data can be loaded into the microprocessor by a detachable data medium. The system also includes a detector associated with each compartment and the memory records the withdrawal of pills from each compartment and the microprocessor includes a counter responsive to the detector for counting down the pills dispensed from the compartment so that the patient is able to determine the remaining number of medications in each compartment. The compartments are selectively detachable from the dispenser and the dispenser's controller is capable of determining how many compartments are engaged with the dispensers housing.

While all of the above medication dispensers provide various levels of alerts and monitor the dispensing of medication to various degrees, there remains a need in the art for a medication dispenser with an improved reminder system.

BRIEF SUMMARY OF THE INVENTION

A medication reminder and compliance system including a pill box, a pill box and electronic device; or a pill box, electronic device and remote server is disclosed. The pill box includes several detachable dosettes, each of which is divided into several chambers and includes its own a door. A two-color LED is disposed beneath each chamber and is activated when a specific reminder time is reached. The LED initially illuminates the associated chamber from below with a green light but changes to a flashing red light if the door is not opened within a preset time. A sound preferably is also generated when the LED switches from green to red. A switch engaged with the door deactivates the LED when the door is opened. The electronic device communicates with the pill box and alerts the patient when it is time to take medication. The electronic device may be a cell phone, personal computer, a tablet, a pager or any other similar communication device accessible by the patient. One or both of the electronic device and the pill box issues an alert to the patient to let them know that the time has arrived to take a particular dose of medication from a particular chamber on a particular dosette. The dosettes may be individually detached from the housing of the pill box to make it easier for the patient to take their medication if they are travelling for a day, for instance. Alerts will still be issued by the electronic device if a dosette is disengaged from the pill box. A remote server which communicates with both the pill box and electronic device can be programmed to control the reminder schedule and monitor the patient's compliance with a prescribed medication regimen.

There is further disclosed a method of utilizing the medication reminder and compliance system to remind a patient to take a dose of a medication in a timely fashion. This method includes the steps of providing an electronic pill box having a housing with a plurality of dosettes disposed therein, where each dosette has one or more chambers defined therein, and each chamber has a door that is movable between an open and closed position; an illumination device positioned to illuminate an underside of the door of each chamber; and a switch operatively engaged with each illumination device;

providing a reminder schedule to a microprocessor in the pill box housing;

loading appropriate chambers corresponding to the reminder schedule of medication with an appropriate dose of a medication;

tracking real time relative to the reminder schedule;

providing a first reminder to the patient to take a particular dose of medication from a particular chamber when the real time corresponds to a time on the reminder schedule.

The step of providing the first reminder includes illuminating the door of the particular chamber with a first color light emitted by the associated illumination device; recording a compliance event when the patient takes the particular dose of medication from the particular chamber; deactivating the illumination device when the associated dose of medication has been taken; and continuing to track time to a next instance where real time corresponds to a scheduled reminder time.

The step of deactivating the illumination device occurs when the door to the particular chamber is opened and this occurs when the door breaks contact with the switch associated therewith when the door is moved from a closed position to an open position.

The method further includes the step of issuing a second reminder to the patient if the door to the particular chamber is not opened within a preset period of time. This is accomplished by changing the light emitted from the illumination device associated with the particular chamber from the first color to a second color and possibly causing the light of the second color to flash. It may also include emitting an audible sound from the housing of the pill box.

If the patient fails to comply and take the medication after the issuance of the second reminder, the method further includes the steps of recording a non-compliance event; deactivating the illumination device; and continuing to track time to a next instance where real time corresponds to a scheduled reminder time.

The method further includes the step of generating a report after completion of taking of the doses of medication loaded into the pill box after completion of the reminder schedule.

Another aspect of the invention includes providing an electronic device accessible to the patient and linking the electronic device to the pill box so that bidirectional communication between the electronic device and pill box is possible. In this instance, the step of providing a reminder schedule to a microprocessor in the pill box housing includes the steps of uploading the reminder schedule to the electronic device; storing the reminder schedule in the electronic device; and transmitting the reminder schedule in whole or in part to the microprocessor. The step of linking the electronic device to the pill box includes connecting the electronic device and pill box to each other utilizing WiFi or Bluetooth technology.

Still further, in this second aspect of the method, the step of issuing either of the first and second reminders to the patient further includes providing an alert to the patient via the electronic device such as by sending the patient one or more of a voice message, an email, a text, a Tweet®, a Facebook® post, a push notification or a pager notification. The patient can record a compliance event by responding on the electronic device to the alert provided to them or simply by opening the door to the appropriate chamber on the pill box.

In yet another aspect of the method there are also include the steps of providing a remote server; and electronically linking the remote server to one or both of the electronic device and the pill box. In this instance the method also includes entering data relating to the patient and to the reminder schedule into the remote server; and controlling the reminder schedule from the remote schedule. The data may be entered into a dedicated website operatively linked to the server into a dedicated electronic medical server (EMR); and then syncing the EMR with the server.

The method further includes the option of electronically linking a caregiver's electronic device with the server; and contacting the caregiver via their electronic device if the patient fails to take the particular dose after issuance of a second reminder. The server may also be linked to multiple sets of patients' pill boxes, patients' electronic devices; and caregivers' electronic devices so as to monitor multiple patients simultaneously.

BRIEF DESCRIPTION OF THE SEVERAL VIEWS OF THE DRAWINGS

A preferred embodiment of the invention, illustrated of the best mode in which Applicant contemplates applying the principles, is set forth in the following description and is shown in the drawings and is particularly and distinctly pointed out and set forth in the appended claims.

Similar numbers refer to similar parts throughout the drawings.

DETAILED DESCRIPTION OF THE INVENTION

Figure 18:
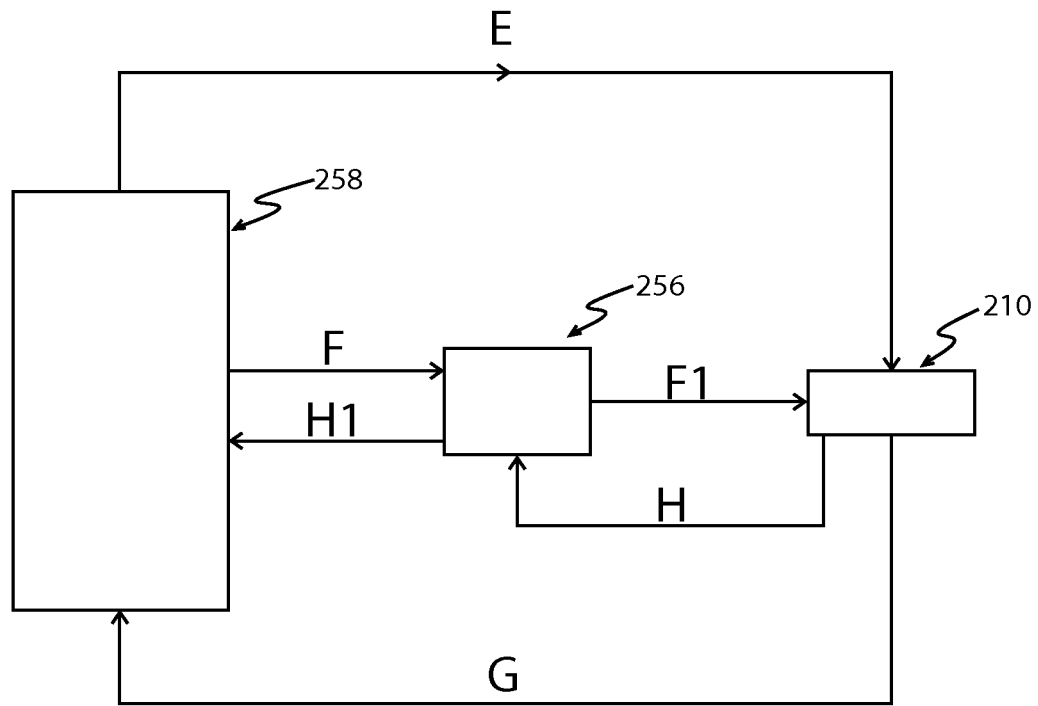
FIG. 18 is a schematic drawing of a third embodiment of the medication reminder and compliance system showing a server, a patient's electronic device, and the electronic pill box.
Figure 19:
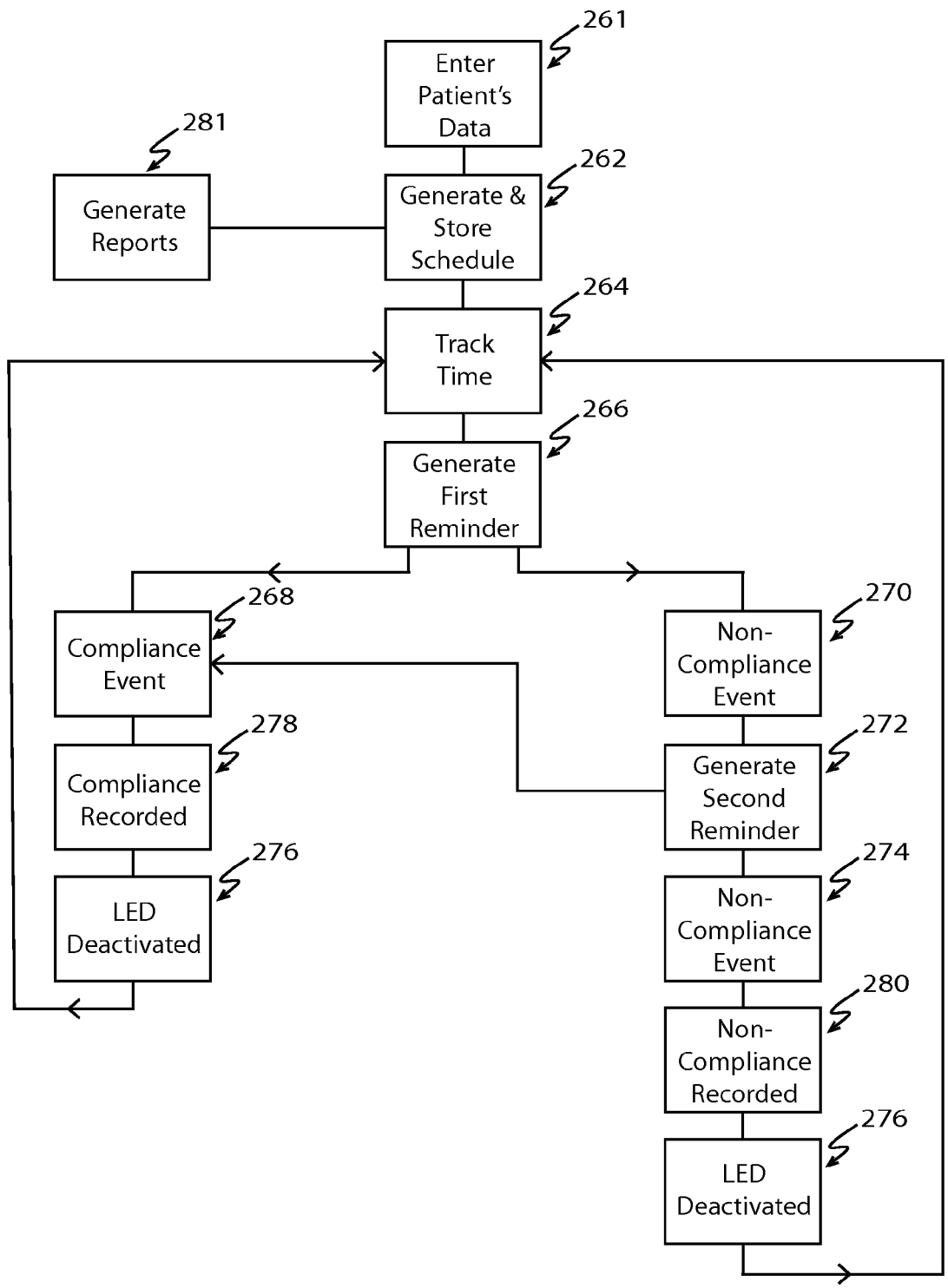
FIG. 19 is a flow chart showing the third embodiment of the medication reminder and compliance system in use.
Figure 20:
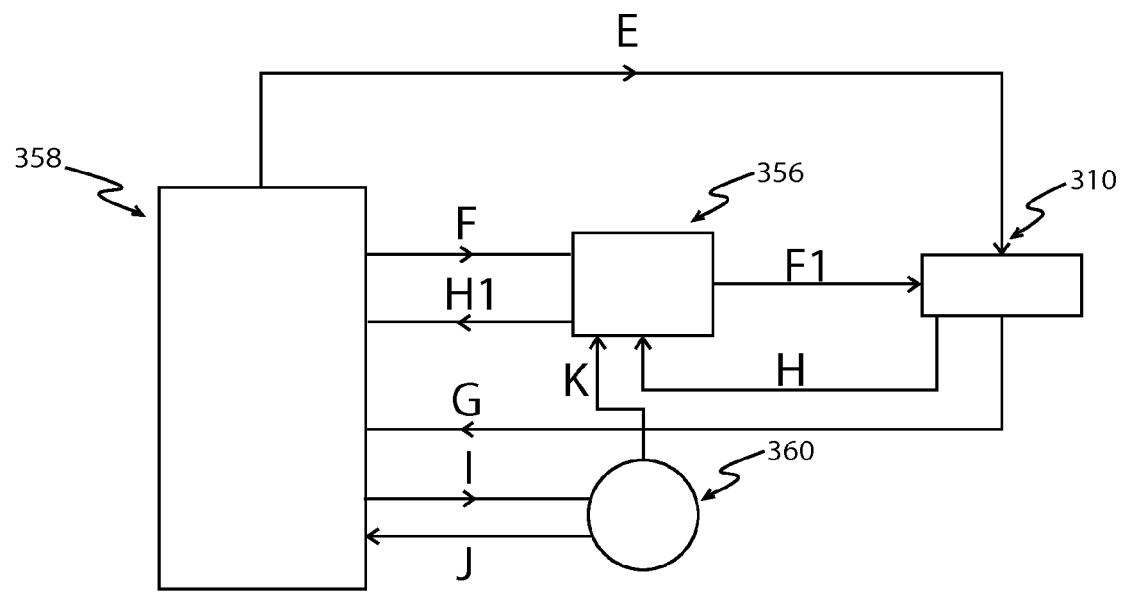
FIG. 20 is a schematic drawing of a fourth embodiment of the medication reminder and compliance system showing a server, a patient's electronic device, the electronic pill box, and a caregiver's electronic device.
Figure 21:
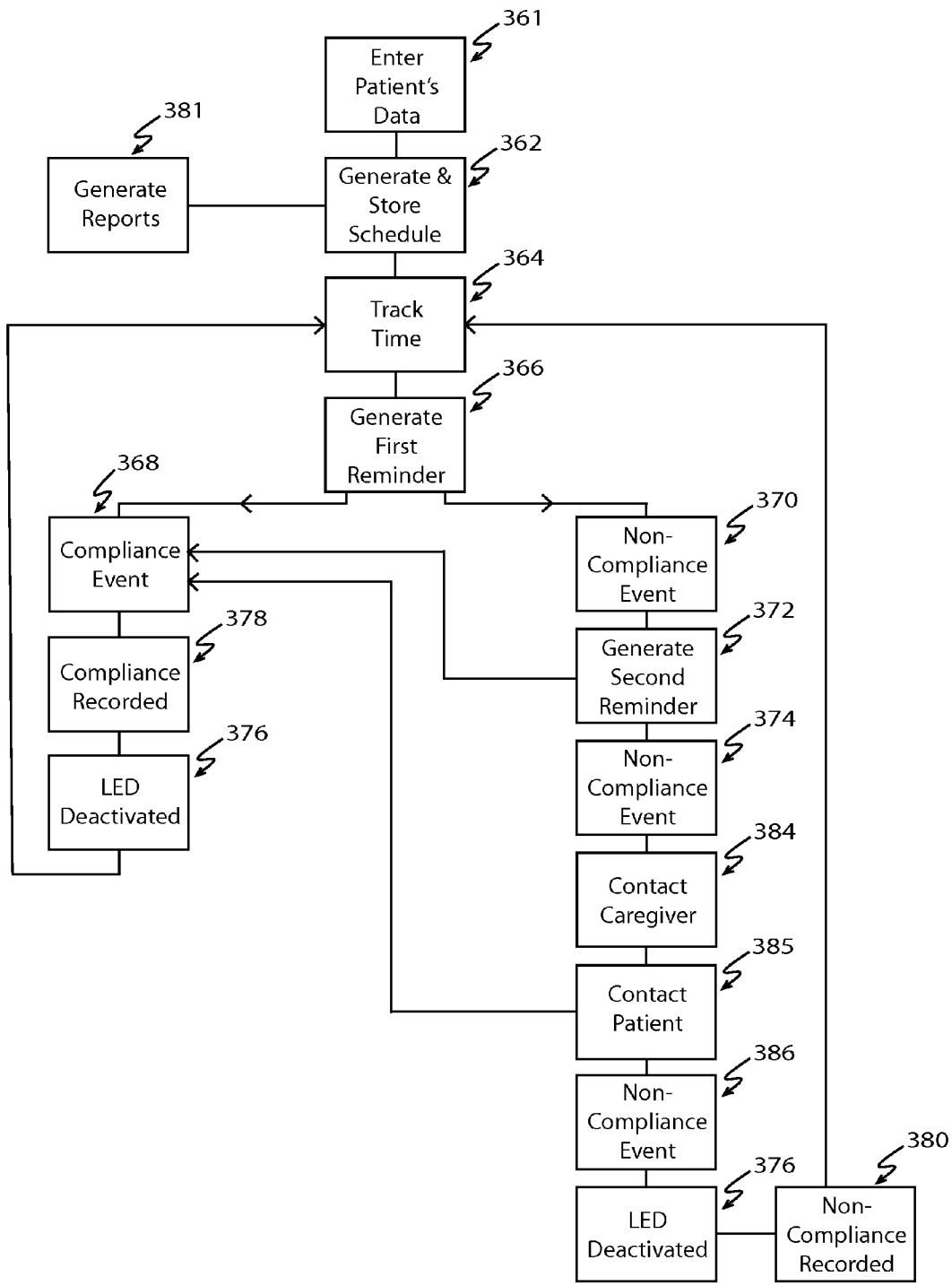
FIG. 21 is a flow chart showing the fourth embodiment of the medication reminder and compliance system in use.
Figure 22:
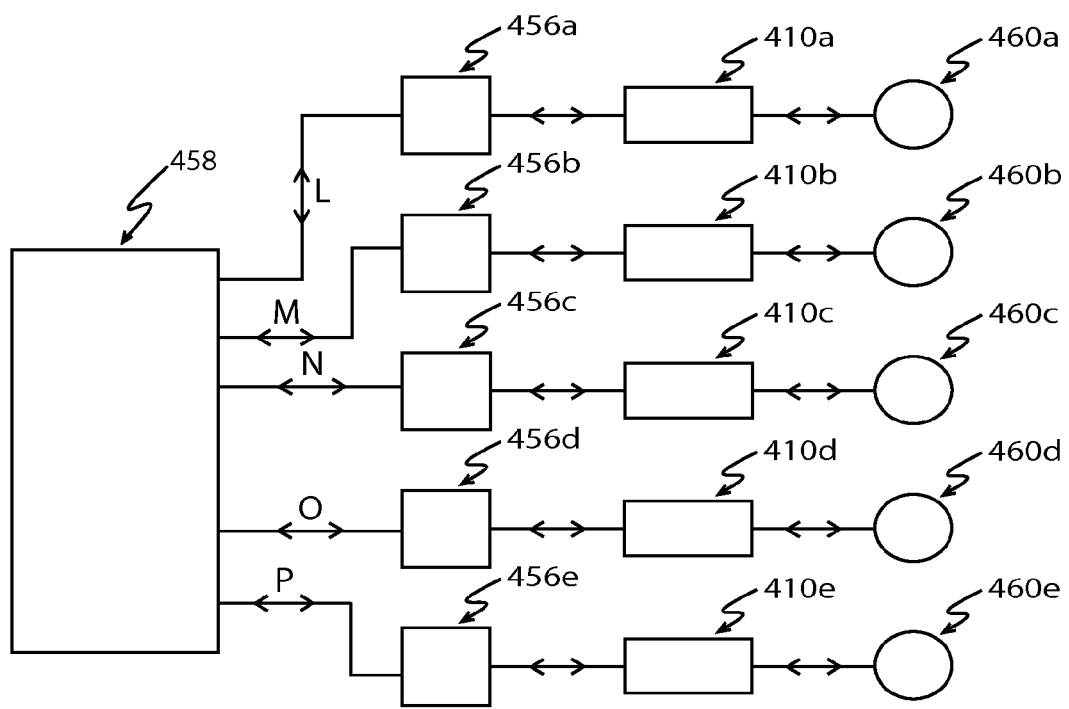
FIG. 22 is a schematic drawing of a fifth embodiment of the medication reminder and compliance system showing a server, several patients' electronic devices and electronic pill boxes; as well as several caregivers' electronic devices.

Referring to FIGS. 1-13 there is shown a first embodiment of a medication reminder and compliance system that includes a first embodiment of an electronic pill box in accordance with an aspect of the present invention, generally indicated at 10. Preferably, pill box 10 is a compact portable device. FIGS. 14-17 show a second embodiment of a medication reminder and compliance system that includes a second embodiment of an electronic pill box in accordance with another aspect of the present invention along with an electronic device accessible by the patient. FIGS. 18 and 19 show a third embodiment of a medication reminder and compliance system which includes a server, the electronic pill box 10 or 110, and a patient's electronic device. FIGS. 20 and 21 show a fourth embodiment of a medication reminder and compliance system which includes a server, the electronic pill box 10 or 100, a patient's electronic device, and a caregiver's electronic device. FIG. 22 shows a fifth embodiment of a medication reminder and compliance system which includes a server, electronic pill boxes 10 or 100 for a plurality of patients, a plurality of patients' electronic devices, and a plurality of caregivers' electronic devices.

In this description the terms "medicine", "medication", "pill", and "pharmaceutical" will be used to describe any preparation (solid, liquid or gel in nature) which is placed by a patient, a caregiver or healthcare professional into the pill box 10, 110 in accordance with the various aspects of the invention. It should be understood that these terms are intended to include but are not limited to drugs used to treat disease, maintenance preparations such as birth control pills, vitamins, and other supplements. Preferably, the pill box disclosed herein is used to house pill-type or capsule-type preparations.

Referring to FIGS. 1-12; pill box 10 preferably is designed for retaining pills for an entire week therein and is configured to remind patients of up to four dosage periods a day. It will be understood, however, that the pill box 10 illustrated herein is by way of an example only and the box may be configured for any time period desired. For example, the pill box may be configured to cover less than seven days a week or it may be configured to cover more than a single week, perhaps even as long as a month. Still further, instead of pill box 10 being configured to cover a plurality of days, the box may be configured to simply cover a twenty-four hour period in order to serve as part of a reminder system for patients who are on a more complex daily regime where medications have to be taken several times in a single day.

Pill box 10 comprises a housing 12 into which seven individual dosettes 14 are separately engaged. Dosettes 14 are engaged with housing 12 in such a way that they may each be removed from housing 12 for travel, for instance, and later re-engaged with housing 12.

Housing 12 has a top wall 12a, a bottom wall 12b, a front wall 12c, a rear wall 12d, a first side wall 12e, and a second side wall 12f. Walls 12a, and 12-12f preferably are molded as a unitary component and bottom wall 12b is subsequently engaged therewith. Housing 12 is fabricated from a suitable material such as Acrylonitrile Butadiene Styrene (ABS) plastic.

Figure 4:
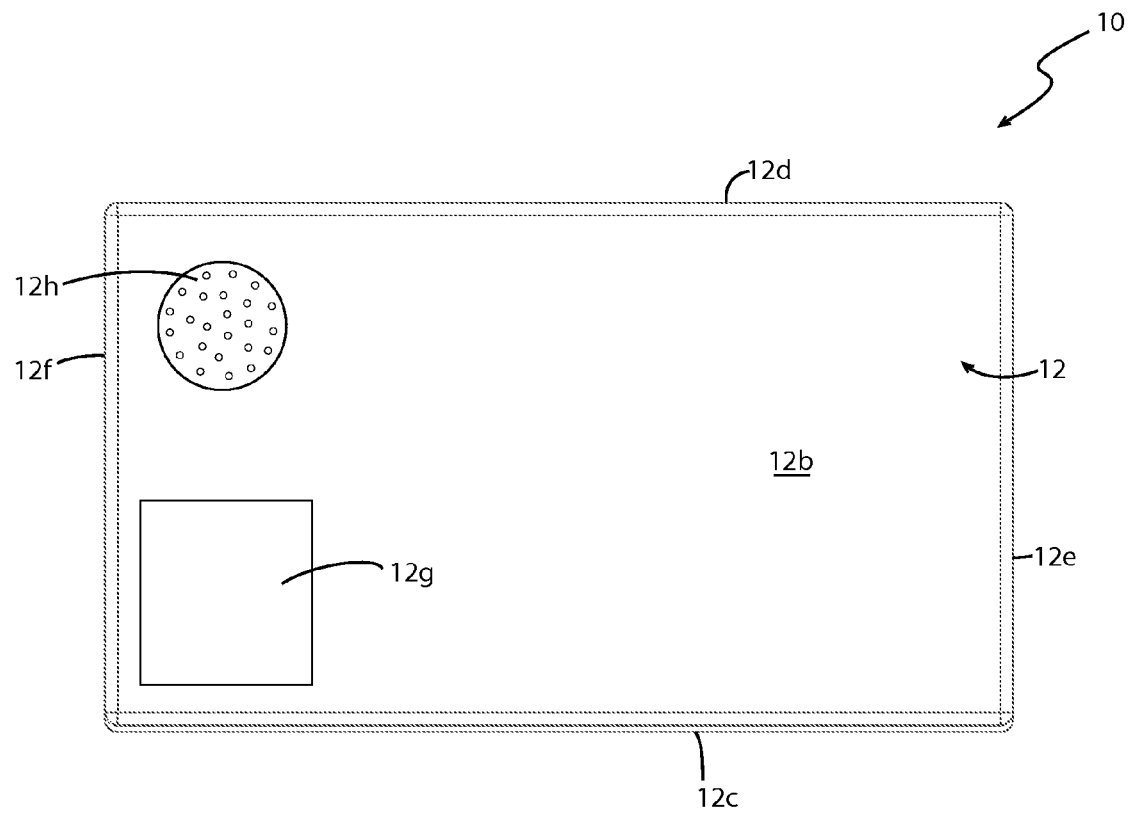
FIG. 4 is a bottom view of the pill box.
Figure 5:
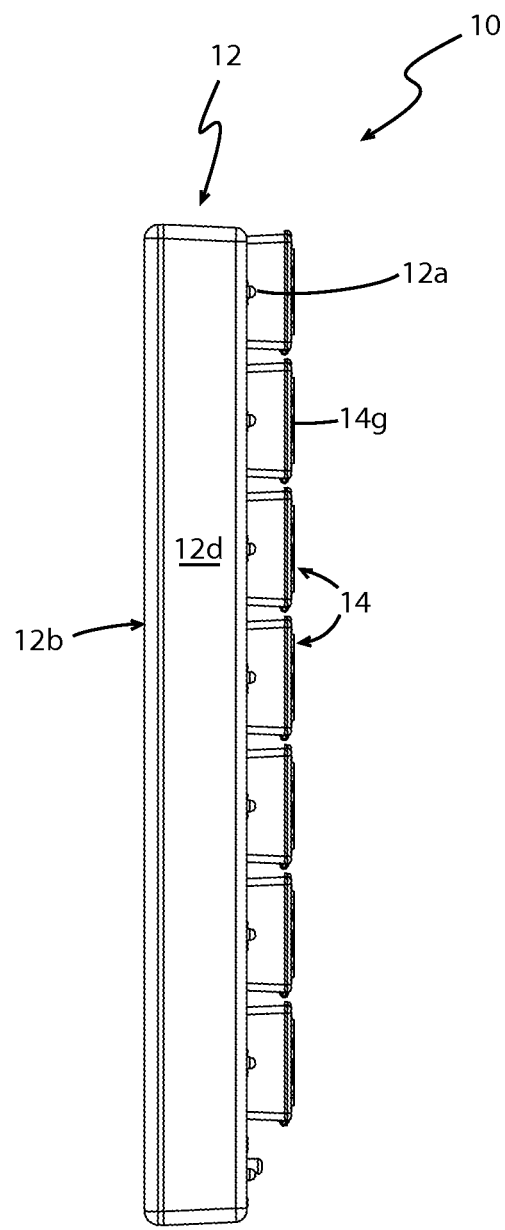
FIG. 5 is a first side view of the pill box.
Figure 6:
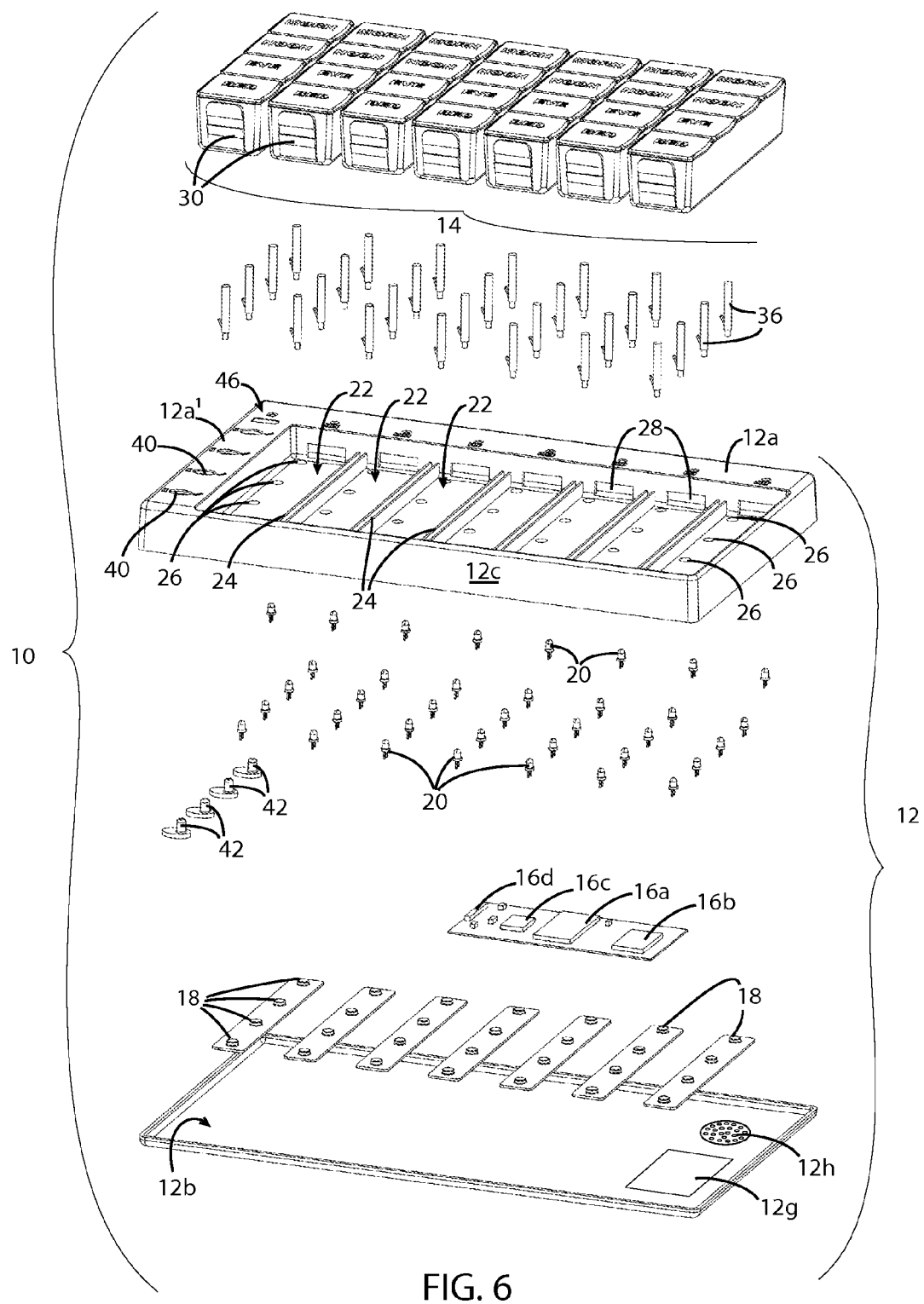
FIG. 6 is an exploded view of the pill box.

Walls 12a-12f bound and define an interior region (not shown) in which is housed a printed circuit board (PCB) 16, a plurality of carbon puck modules 18, and a plurality of two-color LEDs 20 (FIG. 6). Additionally, although not illustrated herein, housing includes a battery compartment, accessible through any of bottom wall 12b or side walls or end walls 12c-12f by removing a cover. An exemplary cover 12g (FIG. 4) is illustrated in FIG. 4 but it will be understood that the battery compartment may be accessible through any of the other walls in housing 12. One or more batteries (not shown) are placed in the battery compartment to provide power to pill box 10. Pill box 10 may be powered in an alternative manner such as by being connected to an external source of AC power by way of a cable (not shown).

A plurality of recesses 22 is defined in top wall 12a of housing 12. Because pill box 10 is configured to be a weekly reminder system, there are seven recesses 22 defined in top wall 12a, one recess for each day of the week. Adjacent recesses 22 are separated from each other by dividing walls 24. One of the carbon puck modules 18 is positioned within the interior of the housing 12 so that it is aligned with a floor region of one of the recesses 22. Preferably, LEDs 20 are two-color LEDs, being capable of selectively emitting a green light and a red light. Each of the LEDs (light-emitting diodes) 20 is operatively engaged with a contact plate 18a of the puck module 18. Each LED 20 is disposed beneath a bottom wall of the associated chamber 32. When the LED 20 is activated, as will be hereinafter described, light is emitted therefrom and shines upwardly through a hole 26 defined in the floor region of the recess 22 and onto a portion of the bottom wall of one of the dosettes 14. Thus, LED 20 will illuminate a chamber 32 within dosette 14 from below. It will be seen from FIG. 6 that a plurality of holes 26 is defined in the floor region of each recess 22. Preferably, four holes 26 are defined in the floor region of each recess 22 and thus there are four LEDs that are capable of illuminating regions of the bottom wall of each dosette 14, as will be further described herein.

The portions of upper wall 12a which define each recess 22 are provided with a locking mechanism 28 disposed in such a position that they are disposed at each of an upper end and lower end of the recess. Locking mechanism 28 is configured to interlocking engage with a tab 30 provided on each end of dosette 14. Locking mechanisms 28 and tabs 30 interlockingly engage each other and thereby securely retain that dosette 14 in the associated recess 22. The uppermost ends of tabs 30 are engaged by the patient's index finger and thumb and are pushed inwardly to disengage tabs 30 from locking mechanisms 28 and thereby release or detach dosette 14 from housing 12. Microprocessor 16a is programmed to recognize that a complete dosette 14 has been detached from housing when all of the activation pins 36 associated with that particular detached dosette 14 have substantially simultaneously disengaged. Microprocessor 16a thus is able to differentiate between the disengagement of a single activation pin 36 (which signifies the opening of a door 14g to a particular chamber 32) and the disengagement of all of the activation pins 36 of a single dosette 14 (which signifies the dosette has been disengaged from housing 12). When a scheduled reminder time arrives for the chambers on the removed dosette 14 microprocessor 16a will not illuminate any of the LEDs 20 associated with that removed dosette and will not sound the audible alarm.

When it is desired to return the removed dosette 14 to housing 12, the dosette 14 is positioned in the correct orientation with respect to the recess 22 from which it was removed and the dosette 14 is pushed downwardly until tabs 30 interlockingly engage locking mechanisms 28 on housing 12. Dosette 14 is thus snap-fittingly engaged into housing 12. It will be understood that pill box 10 may be configured to only include one locking mechanism 28 and interlocking tab 30 and simply have a mating ridge and groove on the other end of the dosette 14. Still further, other types of mechanisms for retaining dosettes 14 engaged with housing 12 may be utilized.

Figure 7:
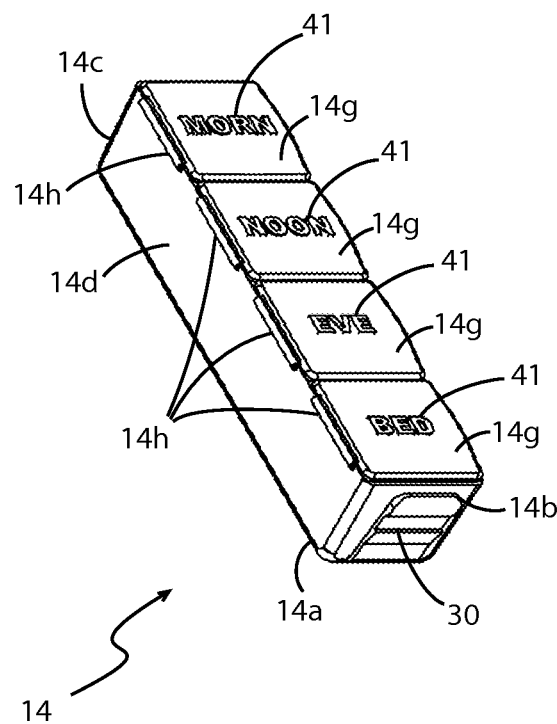
FIG. 7 is a perspective view of one of the removable dosettes detached from the pill box and shown in a closed position.
Figure 8:
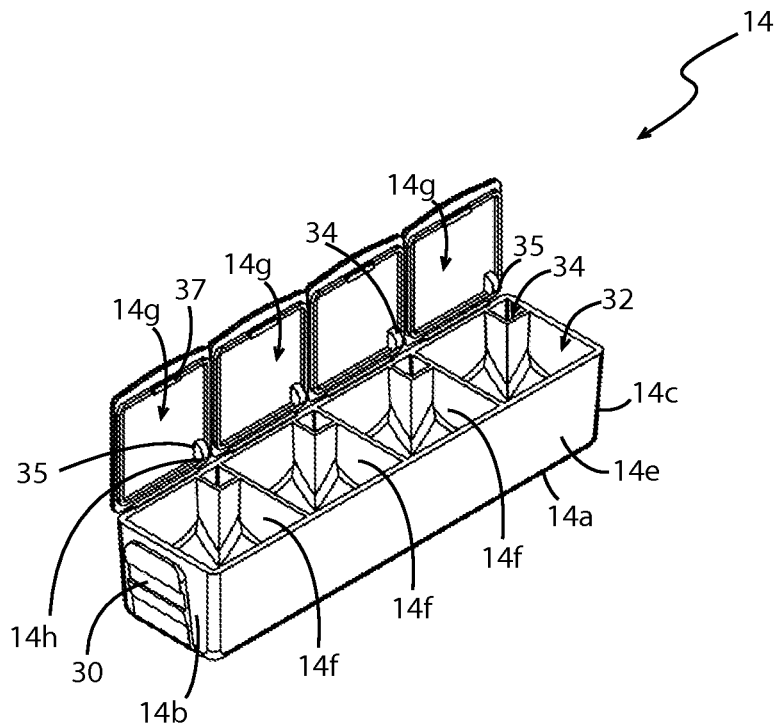
FIG. 8 is a perspective view of the dosette taken from a different angle to FIG. 7 and with the dosette shown in the open position.
Figure 9:
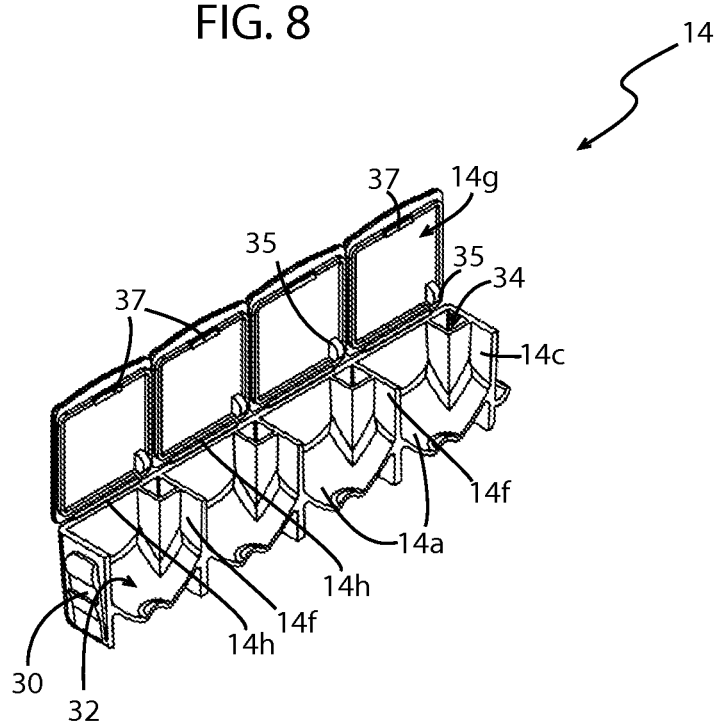
FIG. 9 is a perspective view of the dosette of FIG. 7 shown cut-in half.
Figure 10A:
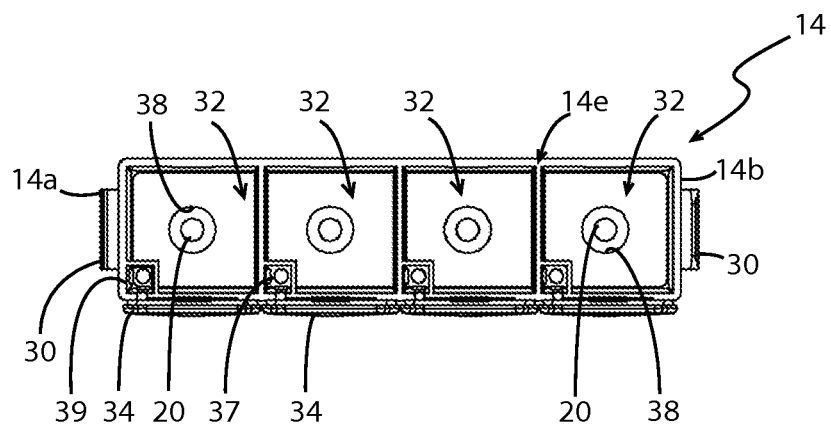
FIG. 10a is a top view of the dosette in the open position.
Figure 10B:
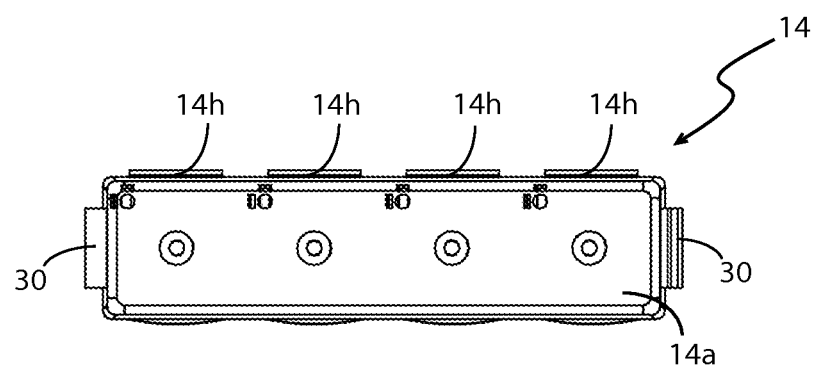
FIG. 10b is a bottom view of the dosette.

In accordance with an aspect of the invention and with particular reference to FIGS. 7-9, each dosette 14 preferably is fabricated from a clear polypropylene and comprises a bottom wall 14a, a front wall 14b, a back wall 14c, a first side wall 14d, and a second side wall 14e. Dosette 14 further includes three dividing walls 14f that are disposed substantially parallel to front and back walls 14b, 14c. Dividing walls 14f are spaced at intervals from each other. Dosette 14 is thus configured into four separate chambers 32 which are each suitable for retaining one or more pills therein.

Each chamber 32 includes a separate door 14g that is engaged with first side wall 14d thereof via a living hinge 14h. Each door 14g is pivotable about its hinge 14h between a closed position (FIG. 7) where door 14g blocks access to an associated chamber 32; and an open position (FIG. 8) where door 14g no longer blocks access to the associated chamber 32. Each door 14g is provided with a latch 37 which engages second side wall 14e and latches door 14g when in the closed position. Fingertip pressure is applied to door 14g is overcome the latching force when it is desired to move door 14g to the open position. When door 14g is moved into the closed position, door 14g must be pushed downwardly by a light force applied by a fingertip and then latch 37 will snap-fit onto the top edge of second side wall 14e. It will be understood that any other suitable latching or locking mechanism may be provided on door 14g of dosette 14. Whatever type of latching or locking mechanism is employed, it preferably is of the type that can be easily operated by sick or elderly patients. In order to remove pills from a particular chamber 32, only the door 14g of that particular chamber 32 is engaged to move it to the open position. The rest of the doors 14g that block access to the adjacent chambers 32 remain in the closed position.

It should be noted that the portion of the bottom wall 14a which forms a bottom wall region of each of the four chambers 32 is rounded so that it is easy to remove pills therefrom with a finger. Instead of lifting the pills out of each chamber 32 with a finger, pill box 10 or dosette 14 (if removed from pill box 10) may be inverted to cause pills to drop out of a selected one of the chambers 32 which has had its door 14g moved to the open position. Dosette 14 preferably further includes at least a transparent, opaque or translucent region 38 in some or all of the bottom wall 14a of each chamber 32. Each region 38 preferably is vertically aligned with one of LEDs 20. Light from the LED 20 will shine through region 38 and illuminate the closed door 14g, as will be further described herein, thereby drawing the attention of the patient to that closed door 14g. Preferably, the entire bottom wall 14a of dosette 14 and some or all of the remainder of the dosette is transparent, opaque or translucent so that the light emitted from LEDs 20 will shine therethrough to illuminate the closed door 14g disposed above an activated LED. Still further, instead of region 38 being opaque or transparent it could be an aperture defined in the portion of the bottom wall 14a and a top end of a LED 20 could terminate in the aperture. Thus light emitted from the associated LED will illuminate the underside of door 14g from within chamber 32.

In accordance with another aspect of the invention, within each of the chambers 32, dosette 14 further defines a smaller compartment 34 that preferably is located in one of the corners of chamber 32. Each compartment 34 is sized to receive an actuator pin 36 (FIGS. 6, 10a, and 10b) therein. Preferably, the actuator pins 36 are fabricated from a suitable plastic material and extend partially downwardly through an aperture 39 (FIG. 10b) in the bottom wall 14a of dosette 14. Each actuator pin 36 is urged by a projection 35 (FIG. 8) on the underside of door 14g downwardly into engagement with a switch (not shown) on PCB 16 when door 14g to chamber 32 is closed. When door 14g is opened the contact between pin 36 and the associated switch is broken. This causes a signal to be generated (as will be discussed later herein) to indicate that door 14g has been opened, presumably because the patient has accessed the medicine retained within chamber 32. It should be noted that the activation pins 36 are essentially the only moving parts in pill box 10.

Figure 3:
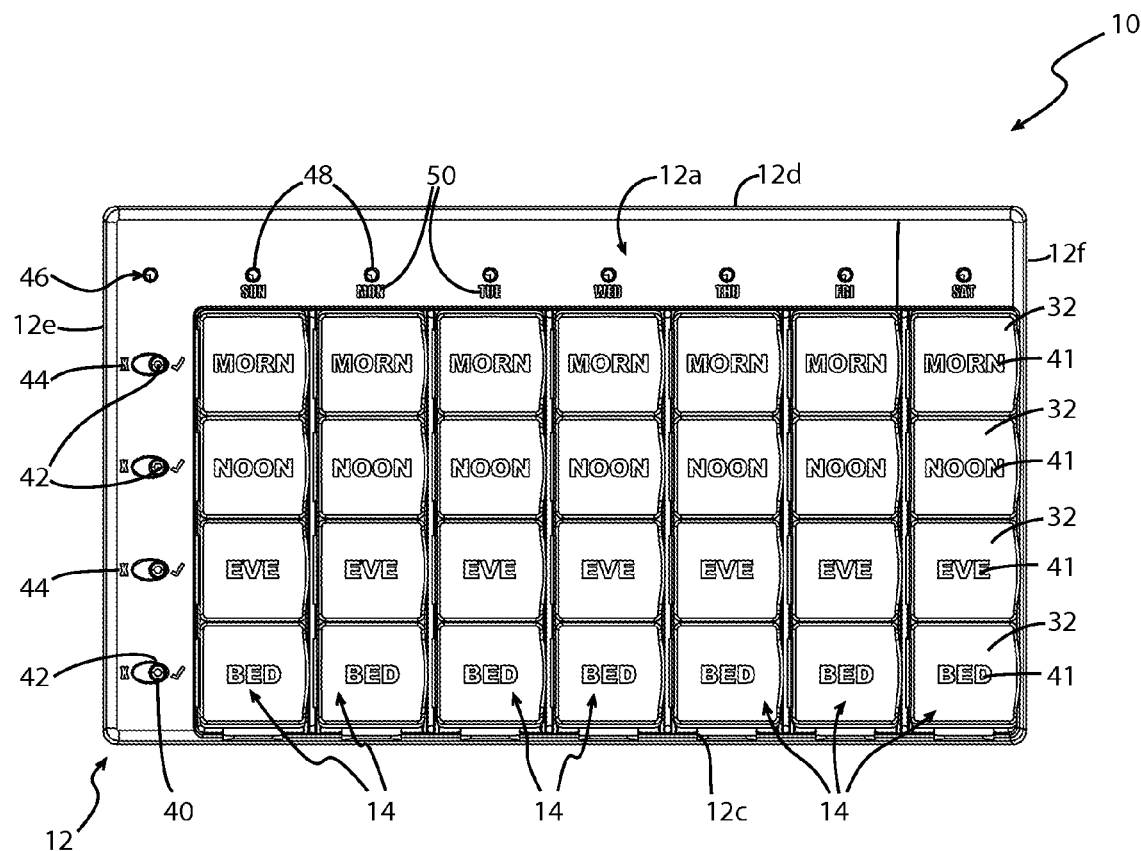
FIG. 3 is a top view of the pill box.

Referring to FIG. 3, it can be seen that the outer surface of each door 14g is provided with indicia 41 thereon. The indicia 41 are markings of some nature which identify the time of day at which a medicine housed within the particular chamber 32 protected by that particular door 14g is meant to be taken by the patient. So, for example, in FIG. 3, a first door 14g is provided with the term "MORN" thereon (representing a time in the morning, preferably around breakfast), a second door 14g immediately below the first door is provided with the marking "NOON" thereon (representing a time around lunchtime); a third door 14g immediately below the second door is provided with the term "EVE" thereon (representing a time around dinnertime); and a fourth door 14g immediately below the third door is provided with the term "BED" thereon (representing a time around bedtime). It will be understood that different indicia may be provided on the doors 14g to indicate either the same time of day as the indicia 41 illustrated in FIG. 3 or a different time of day. A differently configured pill box (perhaps one that includes chambers for each day of a month) would have appropriate different indicia provided on the doors to the various chambers therein.

Figure 1:
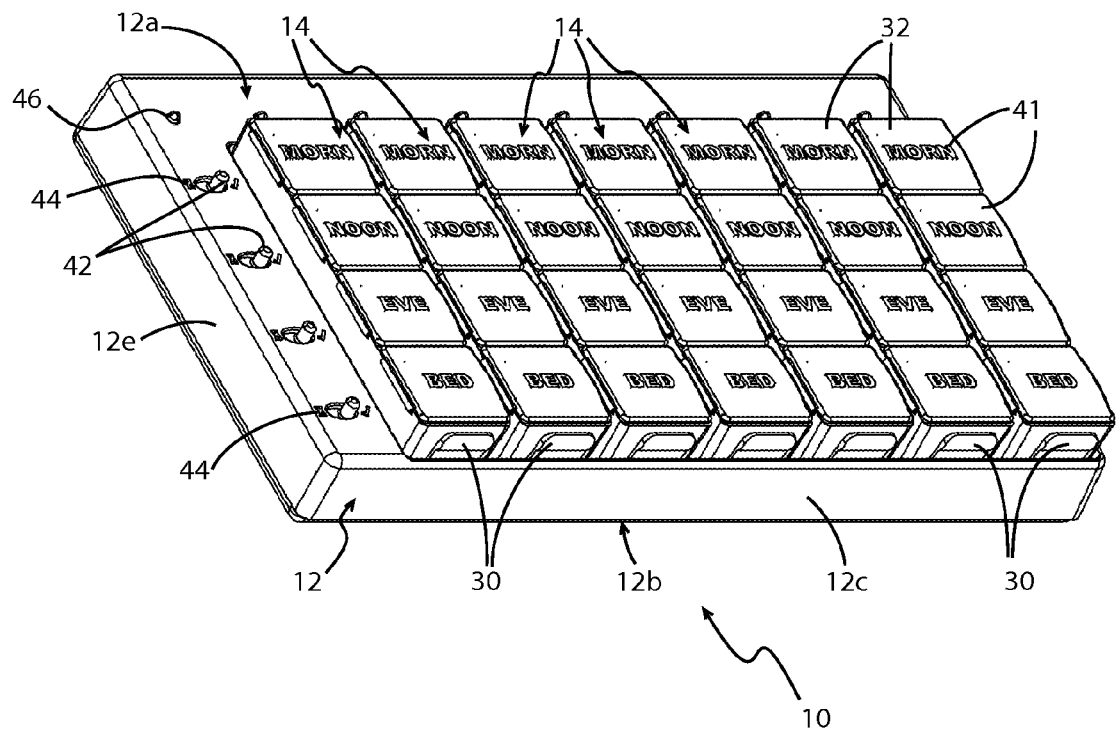
FIG. 1 is a first perspective view of a first embodiment of a medication reminder and compliance system in accordance with an aspect of the invention, said system comprising an electronic pill box that is utilized by a patient.
Figure 2:
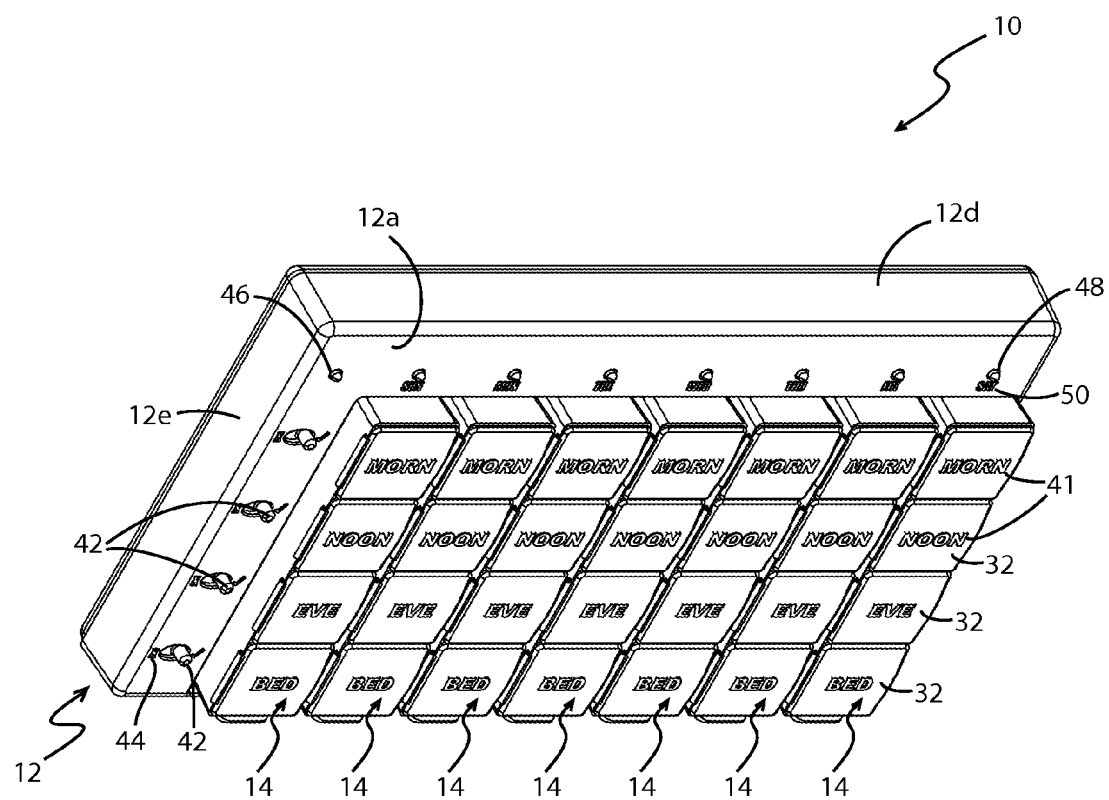
FIG. 2 is a second perspective view of the pill box.

As is evident from FIGS. 1, 3, and 6, a portion of top wall 12a of housing 12 is situated substantially flush or slightly beneath the plane in which closed doors 14g are disposed. In this portion of top wall 12a, referenced by the number 12a' in these figures, there are defined four apertures 40. An event switch 42 extends from the interior of housing 12 through each aperture 40. Each switch 42 is aligned with one of the rows of chambers 32 which extend across the width of housing 12. So, a switch 42 is provided adjacent the row of chambers 32 marked on their doors 14g with indicia 41 which say "MORN"; a second switch 42 is provided adjacent the row of chambers 32 marked on their doors 14g with indicia which say "NOON", etc. In addition to the aperture 40 and associated switch 42 adjacent each row in pill box 10, there is provided a display light 44 to indicate when the switch 42 is activated and/or deactivated. (For example, in FIG. 11a switches 42a, 42b, and 42c are activated and the associated display lights 44 are illuminated. Switch 42d is not activated and the associated light 44 is not illuminated.) Although not illustrated herein it will be understood that LEDs will be provided within the interior adjacent each display light 44.

There is also provided on region 12a', a power display 46. Power display 46 may include a low battery indicator which may include a visual lower battery display or light which displays the level of charge in the batteries housed within the battery chamber (not shown); an on/off button and/or a display light which indicates to the patient whether the pill box is activated or not. (Obviously, if a display light is provided a LED will be provided within the interior of housing 12 adjacent power display 46.) Power display 46 may also be operatively engaged with the sound generation device 16c so that housing sounds an audible alarm if the battery charge is below a certain level.

Finally, a display light 48 is provided on region 12a' above each individual dosette 14 along with a marking 50 which identifies the day of the week the dosette 14 is meant to be utilized. The first dosette 14 is provided with the marking 50 "SUN" to represent the day of the week, Sunday; the second pill dosette 14 is provided with the marking 50 "MON" to represent the day of the week, Monday; the third dosette 14 is provided with the marking 50 "TUES" to represent the day of the week, Tuesday; the fourth dosette 14 is provided with the marking 50 "WED" to represent the day of the week, Wednesday; the fifth dosette 14 is provided with the marking 50 "THURS" to represent Thursday; the sixth dosette 14 is provided with the marking 50 "FRI" to represent Friday; and the seventh dosette 14 is provided with the marking 50 "SAT" to represent Saturday.

Figure 11A:
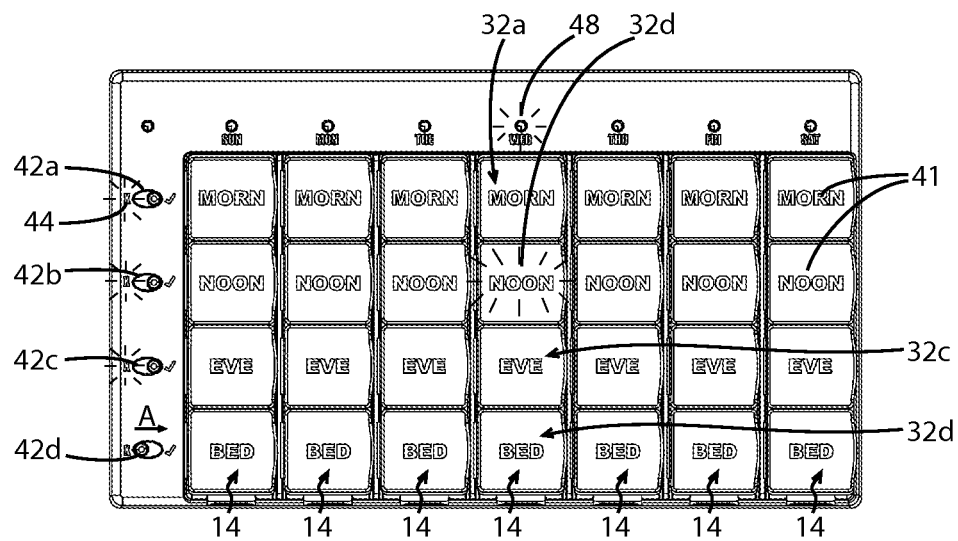
FIG. 11a is a top view of the pill box showing a first one of the chambers in a first one of the dosettes illuminated in a first color to remind the patient to take a first dose of medicine from the illuminated first chamber.
Figure 11B:
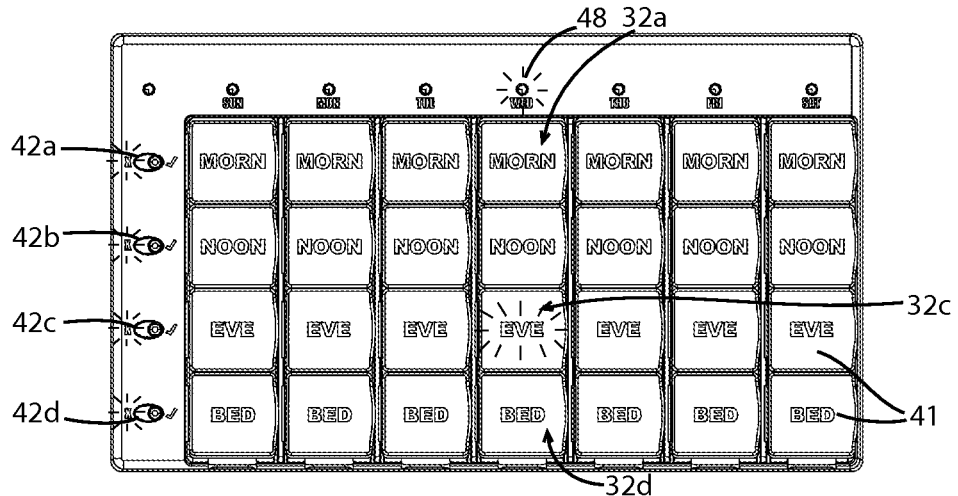
FIG. 11b is a top view of the pill box showing a second subsequent chamber illuminated to remind the patient to take a second dose of medicine from the illuminated second chamber.
Figure 11C:
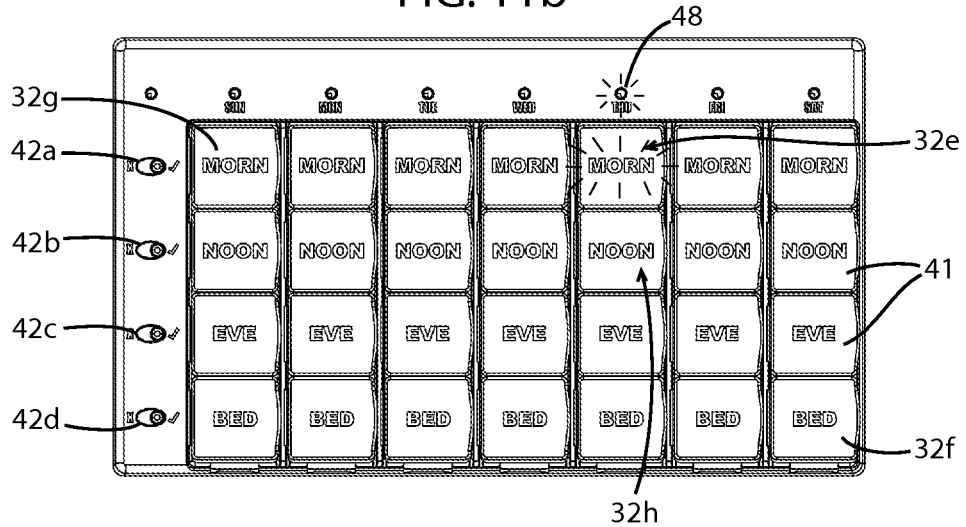
FIG. 11c is a top view of the pill box showing a third chamber in a second dosette illuminated to remind the patient to take a third does of medicine from the illuminated third chamber.

The display light 48 associated with the markings 50 is selectively illuminated to identify which of the dosettes 14 the patient should access on a particular day. So, for example, in FIG. 11a, the fourth dosette 14 associated with the marking 50 "WED" is to be accessed that day and the display light 48 for that day is illuminated. All other display lights associated with the other dosettes 14 are not activated and are therefore not illuminated. In FIG. 11*c*, the fifth dosette 14 with the marking 50 "THURS" is to be accessed that day and the display light 48 associated therewith is illuminated and all other display lights 48 are not illuminated. Thus, it is very easy for a patient to see which dosette 14 they should be withdrawing medication from on any particular day.

The PCB is generally illustrated in FIG. 6 and is fabricated to include a variety of components such as microprocessor 16*a*, a transmitter/receiver 16*b*, a sound generation device 16*c*, and an atomic clock 16*d* and switches (not shown) for operative engagement with actuation pins 36. Although illustrated herein as separate components for the sake of clarity, it will be understood that one or more of transmitter/receiver 16*b*, sound generation device 16*c*, clock 16*d* and switches may instead be features or functions of the programming of microprocessor 16*a* itself. Microprocessor 16*a* is operatively engaged with various components within pill box 10, such as LEDs 20, actuator pins 36, event switches 42, power display 46 and a speaker 12*g* (FIG. 4) for emitting sounds. Transmitter/receiver 16*b* enables communication of pill box 10 with electronic devices 56 that are remote from housing 12—such as cell phones, computers, tablets etc. The transmitter/receiver 16*b* may therefore be a standard cell phone type transmitter/receiver and/or may be WiFi or Bluetooth compatible, or suitable for any other type or communication. Clock 16*d* preferably is an atomic clock that is capable of tracking the real day and time.

The electronic pill box 10 is used in the following manner. If the patient has to take pills four times a day then each of the switches 42 is moved from an off-position to an on-position. FIG. 11*a* shows the switches 42*a*, 42, and 42*c* associated with the "MORN", "NOON", and "EVE" chambers 32 in the on-position. The switch 42*d* associated with the "BED" chamber 32 is in the off-position and needs to be moved in the direction indicated by arrow "A" to move the switch 42*d* to the on-position. When the switches 42*a*-42*d* are moved into the on-position, the associated LED display light 44 is illuminated to indicate to the patient that the switch is in the on-position. This illumination of the display lights 44 associated with switches 42*a*-42*c* is shown in FIG. 11*a*. If the patient is only required to take pills three times a day, then the patient will select the appropriate three event switches 42 and move them from an off-position to an on-position. So, for example, if the patient does not need to take pills at "NOON", they will not move the switch 42*b* adjacent the "NOON" row of chambers 32 aligned with switch 42*b* from the off-position to the on-position. All of the other switches 42*a*, 42*c*, 42*d* will be moved to the on-position. If pills only need to be taken two times a day, then the appropriate two switches will be moved to the on-position and the remaining two switches will remain in the off-position.

When the switches 42*a*-42*d* are moved to the on-position, LEDs 20 aligned with chambers 32 in the appropriate rows ("MORN", "NOON", "EVE" and "BED") are activated and are therefore able to be illuminated at appropriate pre-scheduled times in order to remind the patient to take the medicine contained in the illuminated chamber. The LEDs 20 aligned with any switches 42 which remain in the off-position are not activated and are therefore unable to be illuminated.

Since pill box 10 has an atomic clock therein, microprocessor 16*a* in pill box 10 is able to effectively keep track of the actual day of the week and time of day and will illuminate appropriate LEDs in sequence in accordance with a preset reminder schedule that is either programmed into microprocessor 16*a* or is made available to microprocessor 16*a* (as will be hereinafter described). So, for example, as shown in FIG. 11*a*, if the patient needs to take medication around noon each day and the current day of the week is Wednesday and the time is around "NOON", then microprocessor 16*a* which is operatively connected to the LEDs will cause the LED beneath the "NOON" chamber 32*b* to be illuminated. Since at least a portion of the chambers are made of a clear or opaque material, the light from the LED will shine through chamber 32*b* and will be visible to the patient. Thus, the patient will readily be able to see which chamber should be opened in order to access the appropriate pills. Because the time is around "NOON", the two-way LED 20 will be activated so that it emits a green light. The illumination in combination with the color thereof will let the patient know it is time to take the medication in the illuminated chamber 32*b* and that they are taking the medication is being taken in a timely fashion. If the patient lifts the door 14*g* of that particular chamber 32*b*, then the projection 35 on the underside of door 14*g* will cease to urge actuation pin 36 in that particular chamber downwardly into engagement with an associated switch on PCB 16 and the LED beneath chamber 32*b* goes out.

If, however, the chamber 32*b* is not opened within some pre-determined period of time, the LED associated therewith will switch from emitting a green light to emitting a red light. Thus, the door 14*g* of chamber 32*b* will glow red instead of green. Preferably, the red light will flash to more urgently draw the patient's attention to pill box 10. Additionally, a signal to alert the user will be generated to remind the user to take pills within the chamber 32*b* before the next time event occurs. The signal may take a variety of forms, one of which being a sound that is generated by an appropriate system (not shown) disposed within housing 12. This combination of a visual and audible reminders will hopefully alert the patient to the fact that the need to take the dose of medication from chamber 32*b*. When chamber 32*b* is subsequently opened after the visual and audible reminder, the activation pin 36 associated with chamber 32*b* will disengage from the associated switch on PCB 16 and the LED will be deactivated and cease to emit red light. Chamber 32*b* will therefore no longer be illuminated.

If after even the flashing red light and audible signal have been generated the door 14*g* to chamber 32*b* is not opened, the LED 20 and sound generator will be deactivated after a certain period of time so as not to drain the battery.

As it gets later in the day and approaches the time of day associated with the "EVE" chamber 32*c*, the LED beneath chamber 32*c* will be automatically activated, and the chamber 32*c* will be illuminated with a green light. This is illustrated in FIG. 11 *b*. If door 14*g* associated with chamber 32*c* is opened then the LED beneath the same will be automatically deactivated and the patient will be deemed to have taken the appropriate pills from chamber 32*c*.

The atomic clock will automatically track time and will activate the LED beneath chamber 32*d* when the appropriate preset reminder time arrives. As time continues to move forward, the day of the week will change from Wednesday to Thursday. This will cause the display light 48 above the "THURS" column in pill box 10 to become illuminated, as illustrated in FIG. 11*c*. When the clock reaches the appropriate pre-determined reminder time, the LED beneath the "MORN" chamber 32*e* is activated and illuminates the chamber 32*e* with a green light. Thus, the chambers 32 are illuminated in order sequence along each row and progressively in sequence along the columns. After the final chamber 32*f* in the seventh row (SAT) is illuminated and subsequently opened, the column "SUN" will be activated and the "MORN" chamber 32g will be illuminated at the appropriate pre-scheduled reminder time.

It will be understood that if a patient does not open up a chamber after the LED has switched from illuminating that chamber with a red light and sending an additional signal to the patient, the red LED will go out as soon as the next chamber, such as chamber 32c, is illuminated with a green LED. This is a safety feature built into pill box 10 so as not to tempt the patient to take pills from two chambers, such as chambers 32b and 32c, at the same tire.

It will be understood, however, that pill box 10 may alternatively be configured to keep the red LED illuminated so that the patient is made visually aware that they missed a dose of medication. So, for example, in FIG. 11c if the chamber 32e is not opened, the LED beneath the same will remain red and illuminated even if the LED beneath chamber 32h is activated and glows green. Thus, pill box 10 enables a patient to readily and easily visually determine which dose they need to take next; and the patient can also readily and easily visually determine if they have missed a dose.

Figure 12:
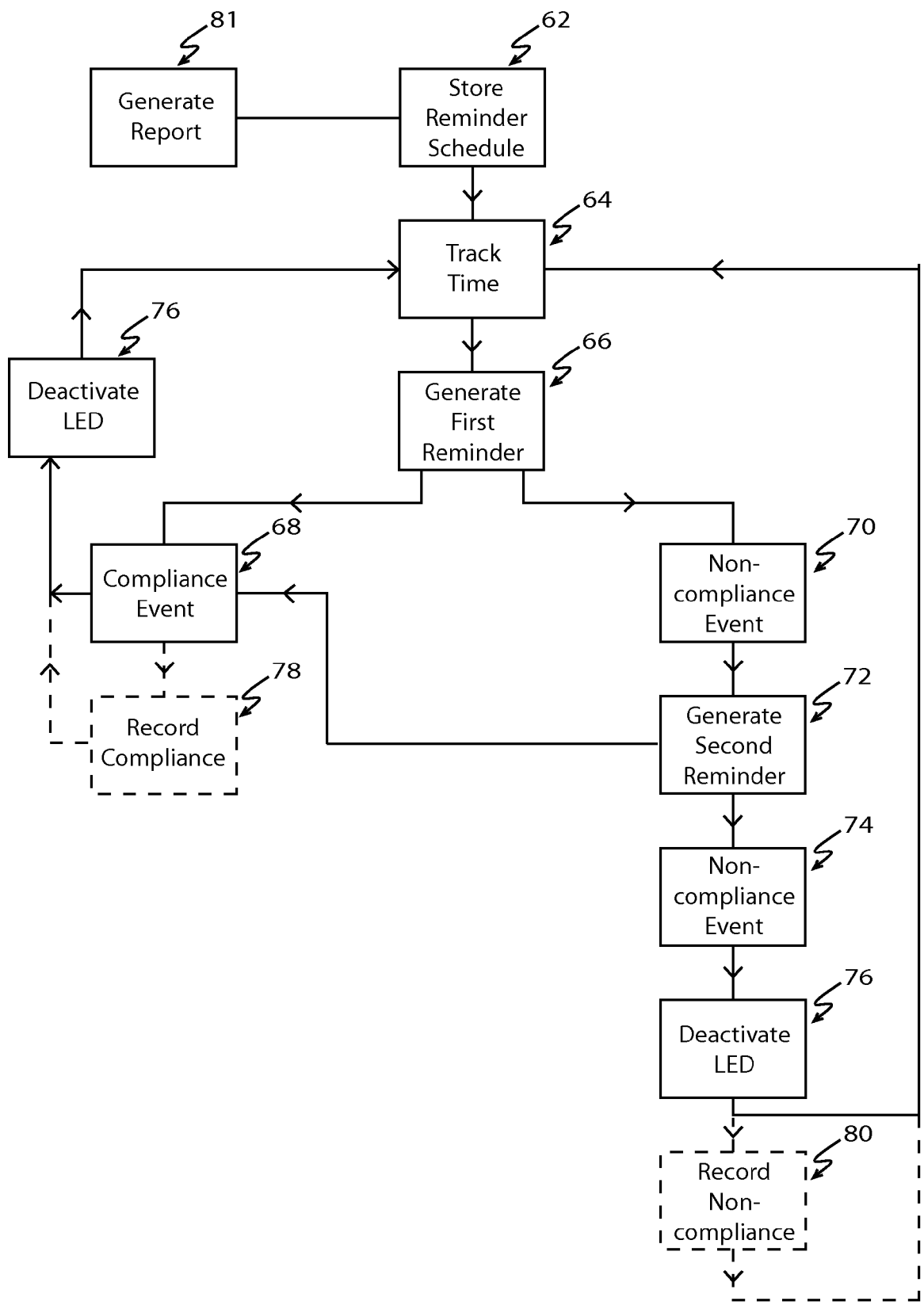
FIG. 12 is a flow chart showing the method of using the first embodiment of the medication reminder system.

FIG. 12 shows a flow chart of the method of using pill box 10 as a medication reminder system. The first step is the providing a reminder schedule to microprocessor 16a within pill box 10. This preferably includes storage 62 of the reminder schedule in microprocessor 16a. Although not illustrated herein, it will be understood that additionally each of the various chambers 32 of pill box 10 associated with the reminder schedule will be loaded with an appropriate dose of medication. The second step is the tracking 64 of the actual day and time and comparing it with a scheduled reminder day and time. The third step is the generation of a first reminder 66 when the actual day and time corresponds with a day and time in the reminder schedule. The first reminder 66 generated is the actuation of a LED 20 disposed beneath a particular chamber 32 on one of dosettes 14 which causes that particular chamber 32 to be illuminated with a green light.

After step three 66 there are two possible pathways that must occur within a preset period of time. In a first instance, the patient opens a door 14g to a particular compartment and consequently a compliance event 68 is registered in microprocessor 16a and the programming reverts to the step of tracking 64. In a second instance, the patient fails to open door 14g to the particular compartment and a non-compliance event 70 is registered in microprocessor 16a. A second reminder 72 is then generated. This second reminder 72 takes the form of the LED 20 being switched from a green light to a flashing red light and/or a sound being generated within pill box 10. Once again there are two possible pathways ensuing from the generation of the second reminder 72. In a first instance, a compliance event 68 is registered and in the second instance, a non-compliance event 74 is registered. The next step is deactivation 76 of the previously activated LED and the programming reverts to the step of tracking 64.

Microprocessor 16a may also be programmed to record the compliance and non-compliance events. The steps of recording these events are shown in phantom in FIG. 12 as steps 78 and 80 respectively. After several scheduled reminder periods have passed, the process may further include the step of generating a compliance report 81. In particular, the compliance report is generated after completion of taking of the various doses of medication loaded into the pill box 10 after completion of the reminder schedule or at any other desired or preset intervals. The report will show the frequency of the reminders issued and the compliance of taking the various doses, or noncompliance, on the part of the patient.

Figure 13:
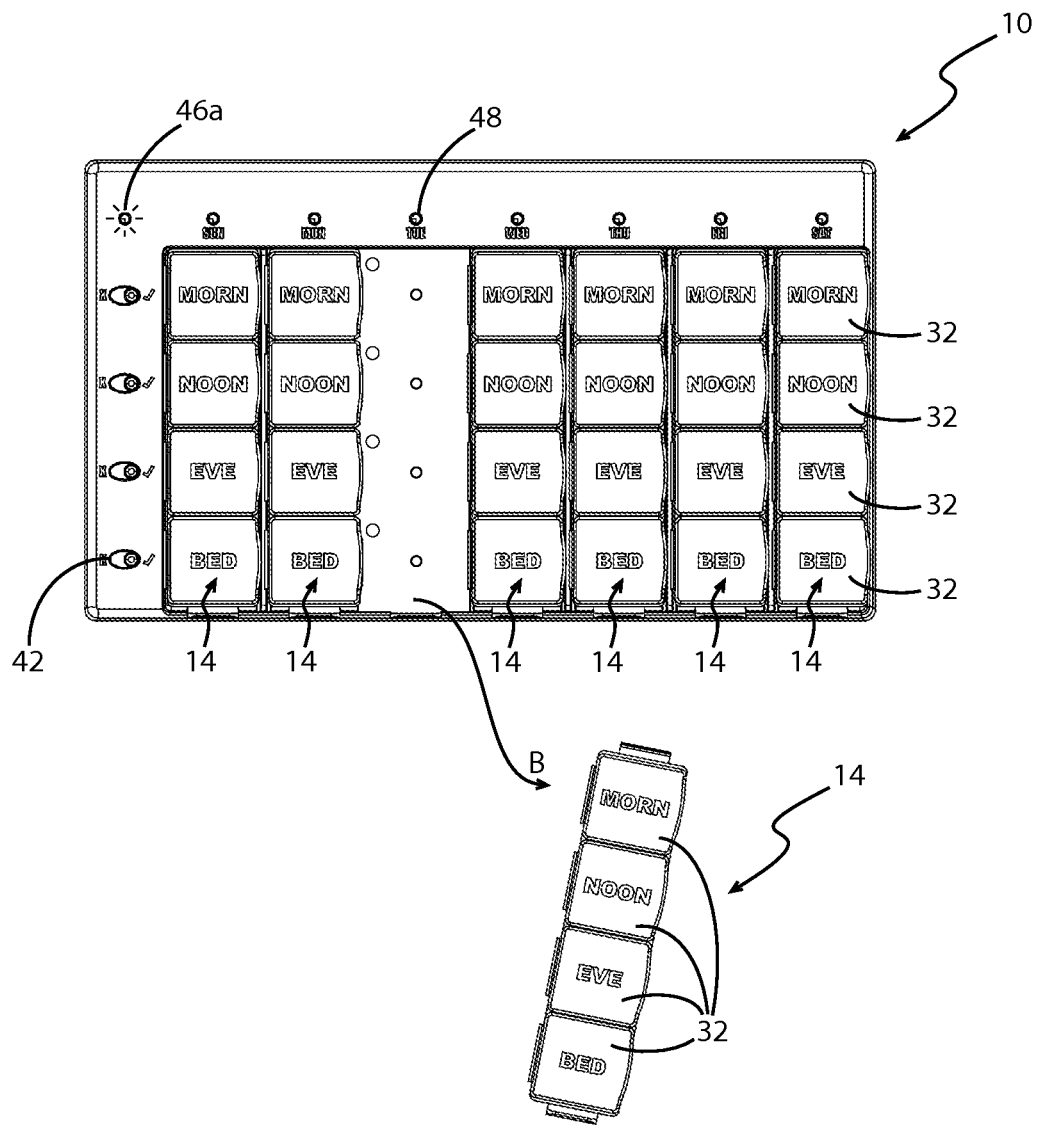
FIG. 13 is a top view of the pill box showing a dosette disengaged from the housing.
Figure 14:
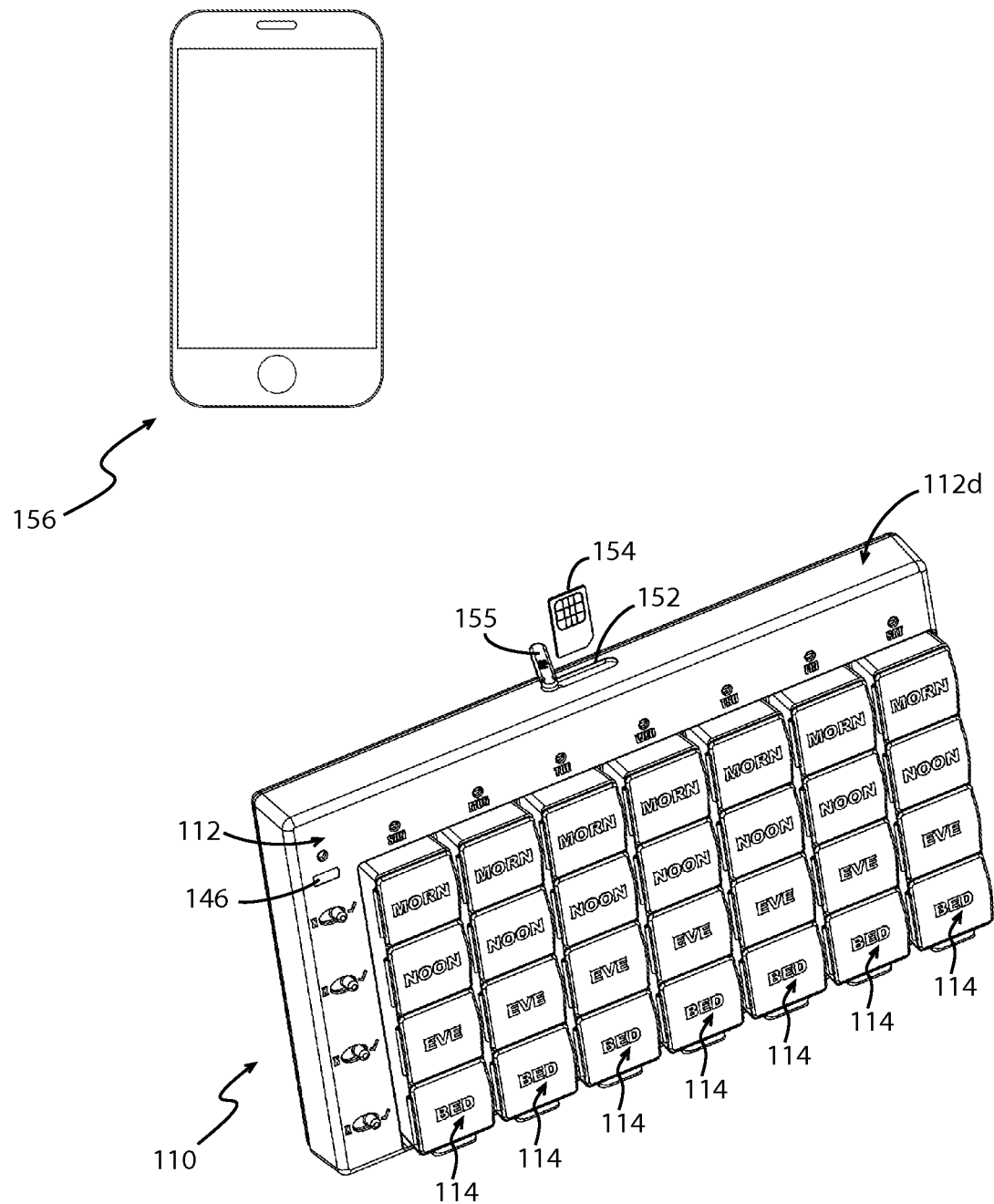
FIG. 14 is a perspective view of a second embodiment of a medication reminder and compliance system in accordance with an aspect of the invention and showing a second embodiment of a pill box utilized therein.
Figure 15:
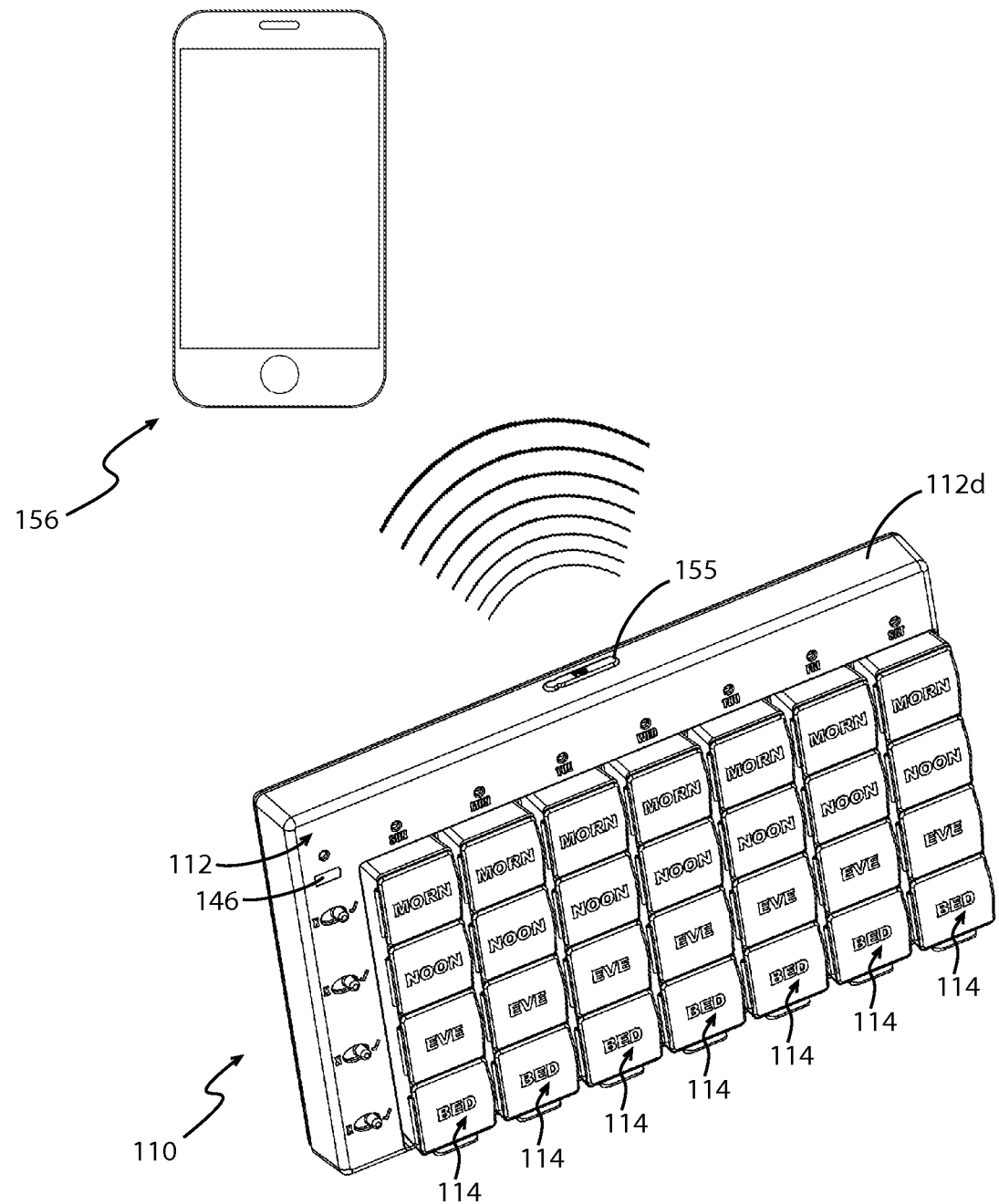
FIG. 15 is a perspective view of the system of FIG. 14 illustrating the box transmitting a signal therefrom.

FIG. 13 shows pill box 10 with one of the dosettes 14 removed therefrom for traveling. In particular, the dosette 14 for pills to be taken on Tuesday has been removed from pill box 10. This action, indicated by arrow "B", breaks the contact between the activation pins (not shown) in dosette 14 and the switches on PCB 16. Consequently, when the time periods on Tuesday are reached, the LEDs which normally would cause individual chambers 32 in dosette 14 to glow will be deactivated. Thus, the pill box 10 does not make any signals (visual or audible) until that dosette 14 is replaced.

Since pill box 10 is powered by batteries (not shown), if the battery on the unit drops below a certain level, the low battery indicator 46a on power display 46 will glow, as is illustrated in FIG. 13. This indicates to the patient that the batteries in the pill box 10 should be replaced or the unit should be connected to a power supply, such as an AC outlet, if appropriate power equipment is provided with pill box 10.

FIGS. 14-17 show a second embodiment of a medication reminder and compliance system in accordance with an aspect of the invention. In this instance, the medication reminder and compliance system includes a pill box generally indicated at 110, and an electronic device 156 accessible by the patient. FIGS. 14-16b illustrate electronic device 156 as a cell phone, preferably a smartphone, but electronic device 156 may be any other type of electronic communication device such as a personal computer, a tablet, or a pager. Preferably, electronic device 156 is provided with programming that is capable of storing and administering a medication reminder schedule that is designed to remind, record and track the compliance with a medication regimen prescribed by a physician or other healthcare professional.

Pill box 110 is substantially identical in structure to pill box 10 except that it additionally includes a slot 152 defined in a portion of the housing 112, such as in side wall 112d. Slot 152 is configured to receive a SIM (Subscriber Identity Module) card 154 therein. A hinged door 155 closes off access to said card 154 when the card is engaged in slot 152. When SIM card 154 is engaged in pill box 110 it is operatively engaged with microprocessor 16a on the PCB (not shown in these figures). SIM card 154 enables bi-directional direct communication with electronic device 156. Pill box 110 and electronic device 156 may be linked together by WiFi or Bluetooth technology or by built-in transmitters and receivers in electronic device 156 and pill box 110. Pill box 110 includes seven selectively removable dosettes 114 that are substantially identical to dosettes 14.

Figure 16A:
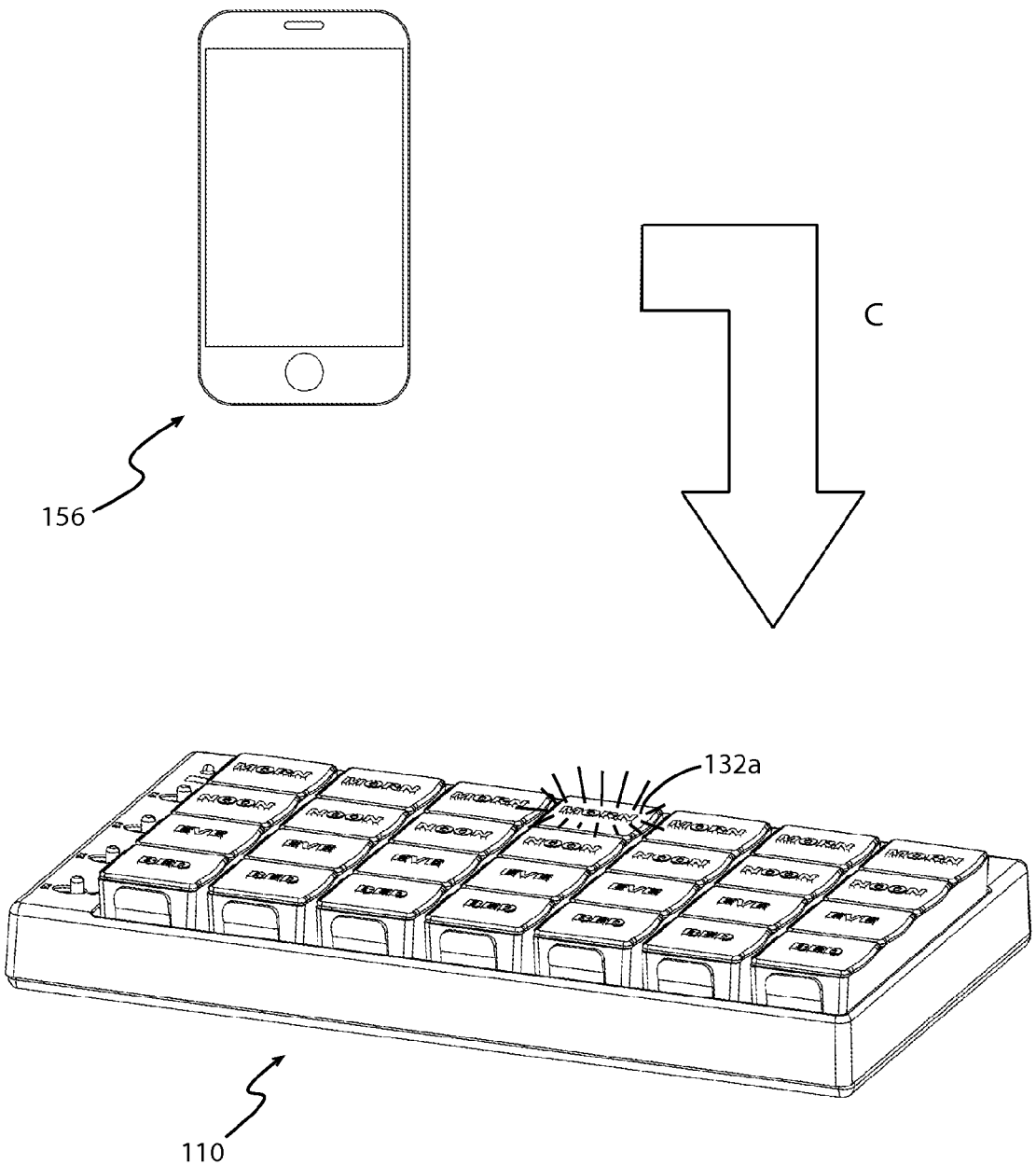
FIG. 16a is a illustrative drawing of the system shown in FIG. 15 showing a signal being sent from the patient's electronic device to the pill box.
Figure 16B:
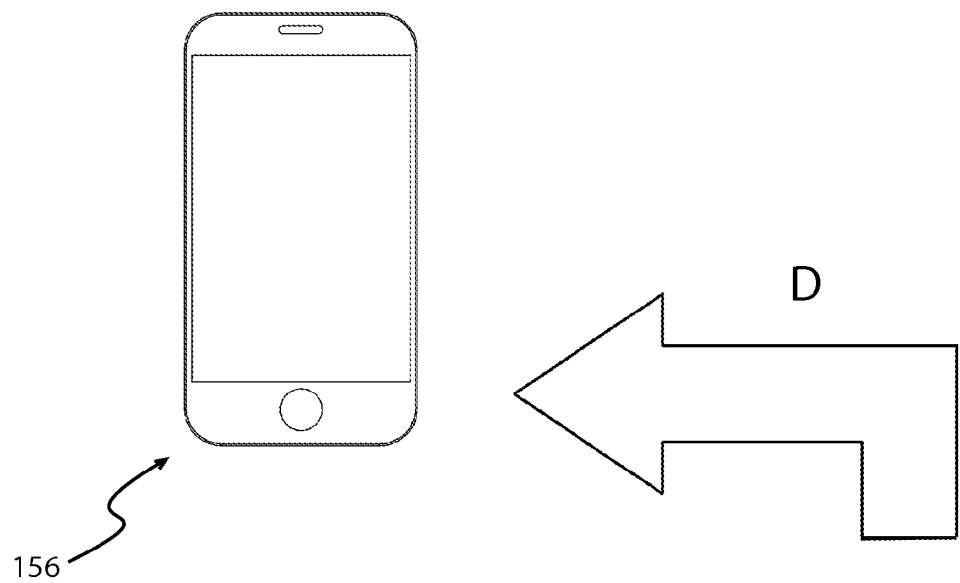
FIG. 16b is a illustrative drawing of the system shown in FIG. 15 showing a signal being sent from the pill box to the patient's electronic device.
Figure 16B:
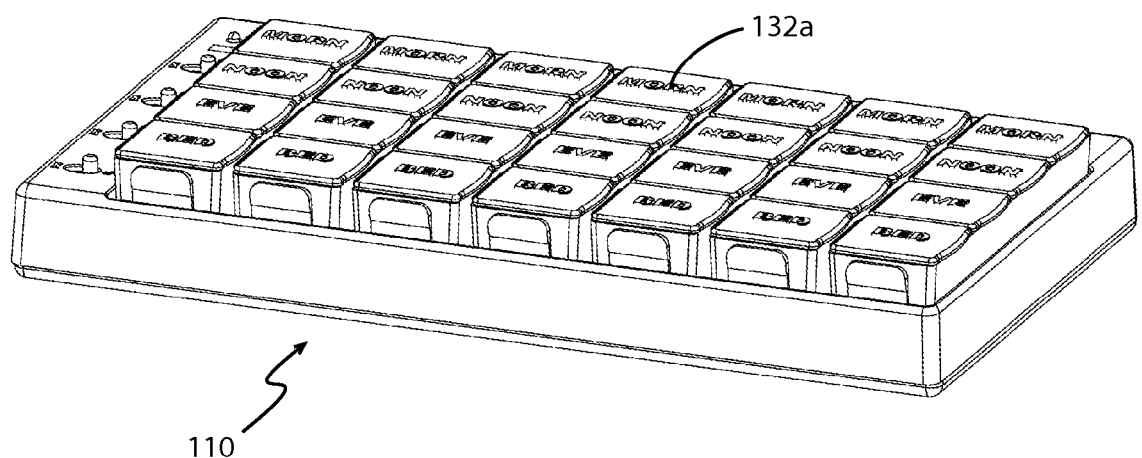

FIGS. 16a and 16b show a signal originating in electronic device 156 being relayed to pill box 110, directing microprocessor 16a therein to illuminate one of the LEDs beneath an appropriate chamber, such as chamber 132a, because it is a pre-scheduled time for a patient to take a dose of medication from chamber 132a. The signal is illustrated in FIG. 16a by the arrow "C". On the actual pill box 110, the chamber 132a is illuminated green by the 2-color LED disposed beneath the chamber in response to receiving this signal. Additionally, electronic device 156 preferably generates a pre-recorded reminder to the patient, on that device, in the form of a voice message, a text message, a Tweet®, an email message, a Facebook® post, a push notification, a pager notification, or any other form of electronic communication that is retrievable by the patient or is accessible to them. In accordance with an aspect of the invention, the system may be set up so that in the communication transmitted to the patient identifies the exact chamber from which the dosage of medication should be removed, what that exact dosage of medication should be and what the pills look like or any other pertinent information.

When the patient opens the door to chamber 132a, presumably to remove the medication retained therein, a signal is sent from pill box 110 to the patient's electronic device 156 to acknowledge the opening of chamber 132a. The signal is indicated by the arrow "D" in FIG. 16b. When the signal "D" is received a compliance event is registered and recorded by electronic device 156, acknowledging that chamber 132a has been opened. The tracking of time continues toward the next scheduled reminder time.

If after the reminder(s) on pill box 110 and/or electronic device 156 have been sent, the illuminated chamber 132a is not opened within a preset time period, a second signal is sent from electronic device 156 to pill box 110 instructing microprocessor 16a to change the LED illuminating chamber 132a from emitting a steady green light to emitting a flashing red light. Pill box 110 preferably also generates a noise to alert the patient that action is needed. Electronic device 156 preferably will also provide a second reminder to the patient in the form of a voice message, email etc. The information that an urgent second reminder was sent is also recorded in electronic device 156 for later review in a compliance report.

If, after the second reminders have been generated, the door to the appropriate chamber is not opened in a preset period of time, the associated LED is deactivated and the tracking of the actual day and time proceeds toward the next scheduled reminder time. A non-compliance event is also recorded for later review in a compliance report.

The system shown in FIGS. 14-17 may be used in a slightly different way. The pill box 110 may function in much the same manner as pill box 10 except that the programming is provided in pill box 110 and not in electronic device 156. The programming in microprocessor 16a in pill box 110 will function in the same manner as programming in pill box 10. When a particular chamber is illuminated when a first reminder is issued, a signal will also be relayed to electronic device 156 to generate a pre-recorded voice message, text message, etc. If the door to the appropriate chamber 132a is opened in a pre-set period of time, the compliance event is registered and recorded by programming in pill box. If after the reminder(s) on pill box 110 and/or electronic device 156 have been sent, the illuminated chamber 132a is not opened within a preset time period, programming in the pill box 110 causes the LED illuminating chamber 132a to change from green to flashing red and a noise may be simultaneously generated. A second electronic signal is relayed from pill box 110 to electronic device 156 to provide a second reminder to the patient in the form of a voice message etc. The information that an urgent second reminder was sent on to the patient's electronic device 156 is recorded for later review in a compliance report. If, after the second reminders have been generated, the door to the appropriate chamber has not been opened, the associated LED is deactivated and the tracking of the actual day and time proceeds toward the next scheduled reminder time. A non-compliance event is also recorded in the pill box's programming.

The accumulated recorded compliance data in either electronic device 156 or pill box 110 which is developed over several scheduled reminder times is able to be compiled into a report that a physician or the patient can review to see if the patient is adequately complying with the treatment regimen they were prescribed.

Figure 17:
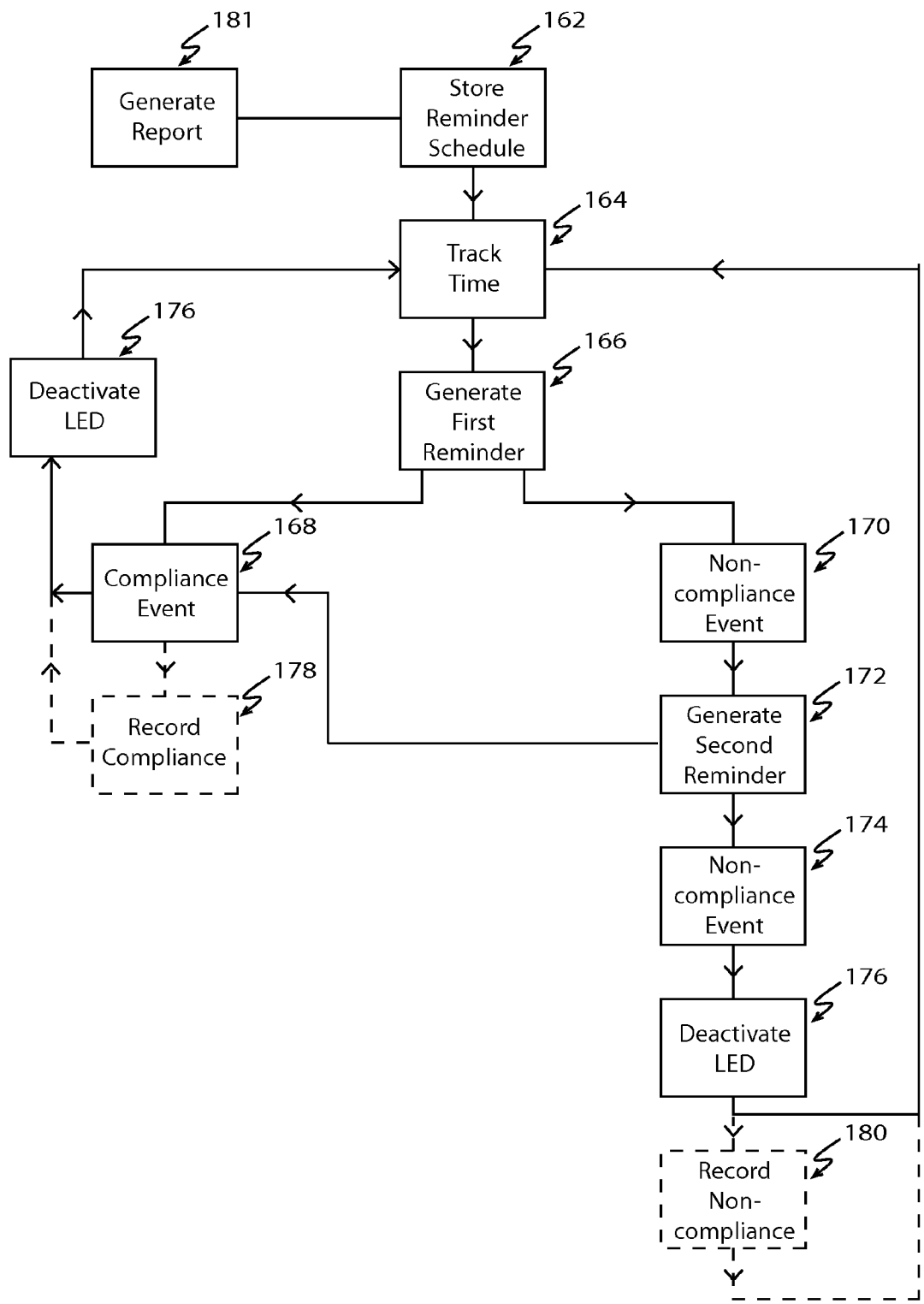
FIG. 17 is a flow chart showing the second embodiment of the medication reminder and compliance system in use.

FIG. 17 is a flow chart showing the method of using the second embodiment of the medication reminder and compliance system. The first step is the storage 162 of a reminder schedule in one of electronic device 156 or pill box 110. In particular, the storage 162 may include providing the reminder schedule by uploading the reminder schedule to electronic device 156, storing the reminder schedule in the electronic device; and possibly transmitting the reminder schedule in whole or in part to the microprocessor within pill box 110.

The second step is the tracking 164 of the actual day and time and the comparison of the actual day and time relative to the scheduled reminder day and time. The third step is the generation of a first reminder 166 when the actual day and time corresponds to the scheduled reminder day and time. As described above, the first reminder includes but is not limited to the emission of a green light by a LED beneath one of the chambers 132 in one of the dosettes 114 and a communication to the patient on their electronic device 156 (i.e., a text message, voice message etc.).

There are two possible pathways after completion of step three 166. The first is registration of a compliance event 168 and the second is registration of a non-compliance event 170. Compliance 168 is determined if door 114g is opened or if the patient clicks a predetermined number or character on their phone; sends a reply email; or takes whatever other steps the first reminder communication instructed them to do to indicate compliance. If there is registration of a compliance event 168 then LED is deactivated 176 and the process reverts to step two, i.e., the tracking of time 164.

If there is registration of a non-compliance event 170, then the next step is the generation of the second reminder 172 as previously described herein. There are again two pathways, namely, the registration of a compliance event 168 or the registration of a non-compliance event 174. If there is registration of a compliance event 168, then the programming reverts to step two 164. If there is registration of a non-compliance event 174 then there is deactivation of the alert signal 176 (i.e., the LED is deactivated) and the programming reverts to step two 164. Once again, the programming may include steps to record the compliance and non compliance events. These recording steps are shown in phantom in FIG. 17 as steps 178 and 180, respectively. After several scheduled reminder periods have passed, the process may further include the step of generating a compliance report 181.

FIGS. 18-19 illustrate a third embodiment of a medicine reminder and compliance system in accordance with an aspect of the present invention. The system is substantially identical to the system illustrated in FIGS. 14-17 except for the inclusion of a server. FIG. 17 is a schematic illustration of this system and shows an electronic pill box 210, an electronic device 256, and a server 258. Pill box 210 may be of any suitable type including but not limited to pill box 10 or pill box 110. Electronic device 256 is again of a type that is accessible to the patient and includes but is not limited to a cell phone, personal computer, tablet, pager, etc. Server 258 may be a server utilized by the patient's physician or may be operated by a third party such as the Applicant whose business it is to provide physicians and other health professionals and pharmaceutical companies with a variety of medical system. Pill box 210, electronic device 256, and server 258 are electronically operatively engaged with each other. In this instance, server 258 is programmed to store and administer the reminder schedule. Server 258 is programmed to include:
  a) a schedule for taking medication on time; and
  b) a reminder system for notifying the patient of the need to take the medication at prescribed intervals; and for repeatedly reminding the patient to do so if the patient is non-compliant after the first reminder; and
  c) a reporting system.

The process for reminding the patient of the need to take their medication and for encouraging compliance is a five-step process which includes:

i) scheduling the prescribed times for taking medication;
ii) reminding the patient of the need to take the medication when one of the prescribed times is reached;
iii) reminding the patient again of the need to take the medication if the patient is non-compliant after step ii); and
iv) reporting the compliance and/or non-compliance events for each prescribed time.

Referring to FIG. 19, the first step in running the medication reminder and compliance system is entering 261 of the patient's data into server 258. Data concerning the patient, the medication and the schedule for taking the medication is entered into server 258 in an appropriate manner. So, for instance, the patient, physician or another healthcare professional, or even a caregiver for the patient, enters the appropriate information into server 258 via a dedicated website. Alternatively, an electronic medical record (EMR) for a patient at their physician's office or in a pharmacy dispensary can be synced with server 258 to transfer the appropriate information thereto. In particular, the patient's consent to be reminded and monitored is entered along with the patient's information regarding the particulars of the electronic device(s) 256 they wish to be contacted on by the system; the information for electronically contacting that electronic device 256 must be entered, (such as a phone number for a cell phone, an email address or an IP address); and the prescribed medication administration times must be entered. The EMR or website programming will generate a reminder schedule and this is uploaded to the dedicated server 258 where it is stored 262. In the case of the data being entered at a pharmacy dispensary or from a doctor's EMR; the entered data is relayed via TCP/IP (Transmission Control Protocol/Internet Protocol) to an dedicated integration module which reads the patient's data and then sends that data on to the dedicated server 258.

The third step in the process is that the programming in server 258 tracks real time 264 and compares the real time relative to a scheduled reminder time stored in the reminder schedule. When the real time and the scheduled reminder time are one and the same, server 258 generates a first reminder 266 and relays that reminder to one or both of pill box 210 electronic device 256. The relaying of this first reminder to pill box 210 is indicated in FIG. 18 by the arrow "E" and to electronic device 256 by the arrow "F". It will be understood that instead of a signal being sent from server 258 to pill box 210, the signal "F" may instead be sent to electronic device 256 which in turn relays a signal to pill box 210 to illuminate the appropriate chamber as previously described herein. This signal is identified in FIG. 17 as "F1". Upon receipt of any of the signals "E" or "F1" in pill box 210, the appropriate LED will be activated and the associated chamber will be illuminated by green light. If server 258 sends the reminder to the patient's phone 256, the patient will receive a text message, voice message, or emails, for example telling them it is time to take their medication.

There are two possible pathways in the system after issuance of the first reminder 266. This is illustrated in FIG. 19. The first pathway is compliance 268 and the second is non-compliance 270. When the patient receives the reminder he or she acknowledges they have received the reminder and taken the required dose of medicine by clicking the text message on their phone to confirm compliance; by selecting a particular specified number on their phone; by clicking a specified link on their phone or computer; or by clicking a specified push notification on their phone. Additionally, opening the indicated door on the appropriate dosette on the electronic pill box will also signal compliance. A compliance signal 268 is relayed from pill box 210 to one or both of electronic device 256 and server 258. The compliance signal to the server 258 is identified by the arrow "G" in FIG. 18 and to the electronic device 256 is identified by the arrow "H". If the signal is sent to electronic device 256, the device 256 will relay a signal back to server 258 and this is identified by the arrow "H1". So, ultimately, the compliance information is relayed to server 258 and is uploaded and recorded 278 in the patient's record to indicate that they complied and took the medication in a timely fashion. It will be understood that any other suitable action format for acknowledging compliance is contemplated to fall within the scope of the present invention. Immediately before or after the compliance event has been recorded 278, the LED is deactivated 276 and the server continues to track time 264 (FIG. 19).

If the door on the appropriate chamber is not opened within a specified period of time, a non-compliance signal 270 is relayed to server 258 and in response, the server will relay a second reminder 272 to pill box 210. This is done to once again try to remind the patient that the time for taking the particular dose of medication has been missed and to urge them to take the necessary action. So, as has been previously described herein, the appropriate LED in pill box 210 will change to emit a red, flashing light and appropriate sounds may be generated by pill box 210. Another text, email or Tweet® or designated type of communication will also be issued by electronic device 256.

After a preset period of time has elapsed since generation of the second reminder 272, there are again two possible pathways, namely compliance 268 or noncompliance 274. If the patient complies 268, then appropriate signals as described above will be relayed to server 258, compliance is recorded 278, LED is deactivated 276, and the server continues to track time 264.

If the patient fails to take the medication yet again, a second non-compliance event 274 will be relayed to server 258 and a non-compliance event will be recorded 280. The LED will be deactivated 276 and the server 258 will continue to track time 264. Periodically, the server 258 will generate compliance reports 281 which can be generated and accessed or sent to the patient, to a pharmacist, a doctor, a caregiver, to an emergency room or other healthcare professional. It is that contemplated that this system will improve a patient's adherence to a treatment regimen and this improve the patient's health.

It should be noted that in accordance with an aspect of this invention, when a patient removes a dosette from pill box 210 for traveling or other reasons, the server will still generate and send a reminder to the patient on their electronic device 256 to take a particular dose at a particular time. The patient will thus still have the ability to confirm they have taken the medication by entering the requisite confirmation on their electronic device 256. The only way that the patient cannot confirm they have complied and taken the required dose of medicine is by opening the door of the chamber on the removed dosette. This is because the dosette has been removed from the pill box 210 and there is therefore no longer any contact between the activations pins and the PCB of the pill box. Consequently, opening the door will not cause a switch on the PCB to trigger and thereby send a confirmation signal to the server 258.

In accordance with another aspect of this invention, the system may be set up so that the server directly programs the pill box's microprocessor 16a with the reminder schedule using standard communication protocols such as WiFi, Bluetooth, etc. When the scheduled reminder time arrives, pill box 210 will illuminate the appropriate chamber and when that chamber is opened by the patient, the compliance event is automatically sent directly from pill box 210 to the server 258. Once again, the compliance by the patient is recorded. If for some reason the pill box is offline, the compliance information is archived in the device and when the pill box goes online again, the server gets updated with the compliance information.

It will be understood that other modifications to the system will be possible. For example, each dosette can include a chip that records when the door thereof is opened if the dosette is removed from pill box 210. Then when that particular dosette is re-engaged with the pill box 210, the compliance information is updated in the pill box 210 and is subsequently or simultaneously relayed to the server 258.

FIGS. 20 and 21 show a fourth embodiment of a medication reminder and compliance system in accordance with an aspect of the invention. This fifth embodiment includes all of the components of the embodiment illustrated in FIG. 18, namely an electronic pill box 310, a patient's electronic device 356, and the server 358, but also includes a caregiver's electronic device 360. The caregiver is a person who possibly has direct contact with the patient and is perhaps a family member or friend, or is a visiting nurse, for example. The caregiver is previously selected and their relevant information is included in the patient information that is entered 361 into server 358. The medication reminder and compliance system functions in the same manner as described with reference to FIGS. 18 and 19 but in this system there is the additional function of escalating and intervening if there is no compliance by the patient after issuance of the second reminder, as will be hereafter described.

Referring to FIG. 21, the method of using the fourth embodiment of the system includes entering patient's data 361 into server 358, generating and storing a medication reminder system 362 in server 358, tracking actual days and times 364 and comparing those days and times with the reminder schedule; generating a first reminder 366 and relaying the same to pill box 310 and electronic device 356. The relaying of this first reminder to pill box 310 is indicated in FIG. 20 by the arrow "E" and to electronic device 356 by the arrow "F". It will be understood that instead of a signal being sent from server 358 to pill box 310, the signal "F" may instead be sent to electronic device 356 which in turn relays a signal to pill box 310 to illuminate the appropriate chamber as previously described herein. This signal is identified in FIG. 20 as "F1". Upon receipt of any of the signals "E" or "F1" in pill box 310, the appropriate LED will be activated and the associated chamber will be illuminated by green light. If server 358 sends the reminder to the patient's phone 356, for example, the patient will receive a text message, voice message, or emails, for example telling them it is time to take their medication.

There are two possible pathways in the system after issuance of the first reminder 366. This is illustrated in FIG. 21. The first pathway is compliance 368 and the second is non-compliance 370. The compliance 368 as indicated in the manner previously described herein. The compliance signal 368 is relayed from pill box 310 to one or both of electronic device 356 and server 358. The compliance signal to the server 358 is identified by the arrow "G" in FIG. 20 and to the electronic device 356 is identified by the arrow "H". If the signal is sent to electronic device 356, the device 356 will relay a signal back to server 358 and this is identified by the arrow "H1". So, ultimately, the compliance information is relayed to server 358 and is uploaded and recorded 378 in the patient's record to indicate that they complied and took the medication in a timely fashion. Immediately before or after the compliance event has been recorded 378, the LED is deactivated 376 and the server continues to track time 364 (FIG. 21).

If the door on the appropriate chamber is not opened within a specified period of time, a noncompliance signal 370 is relayed to server 358 and in response, the server will relay a second reminder 372 to pill box 310 and electronic device 356 as previously described. After a preset period of time has elapsed since generation of the second reminder 372, there are again two possible pathways, namely compliance 368 or non-compliance 374. If the patient complies 368, then appropriate signals as described above will be relayed to server 358, compliance is recorded 378, LED is deactivated 376, and the server continues to track time 364.

If the patient fails to take the medication yet again, the second non-compliance event 374 will be relayed to server 358 and the server 358 will then relay an intervention reminder signal 384 to a caregiver's electronic device 360. This signal 384 is indicated by the arrow "I" in FIG. 20. The intervention reminder will be sent via text to the caregiver's phone, via a voice message to the caregiver's phone, via email to the caregiver's phone or computer; or via push notification, or via a pager notification to the caregiver's pager. The caregiver may relay an acknowledgement signal "J" from their electronic device 360 to the server 358 to indicate they have received the signal "I". The caregiver is then charged with attempting to directly contact the patient 385 to remind him or her to take the medication indicated by pill box 310. The caregiver may send a message from their electronic device 360 to the patient's electronic device 356 as indicated by the arrow "K"; or they may personally talk to the patient. Once again, there are two possible pathways, namely, compliance, 368 and non-compliance 386. If there is subsequent compliance 368 an appropriate signal is relayed back to server 358 in the manner previously described with reference to the system shown in FIG. 18. Alternatively or additionally, the caregiver may send an additional signal "J" back to server 358 to indicate personal knowledge of compliance. The compliance event 368 is recorded 378 in server 356, the LED is deactivated 376 and the server goes back to tracking time 364.

If non-compliance 386 is the result of the caregiver contacting the patient or failing to contact the patient, then the non-compliance event 386 is registered by server 358 and is recorded 380. The appropriate LED is deactivated 376 and the server reverts to tracking time 364. Periodically reports of the compliance results are generated and relayed 381 to one or all of the patient, the physician or pharmacist and caregiver.

FIG. 22 illustrates a further embodiment of a medication reminder and compliance system which comprises a server 458 which is used to remind and monitor a plurality of patient who have been prescribed one or more medications. Server 458 may be dedicated in that it is utilized by a single doctor's office, hospital, or pharmacy or it may be operated by a third party and be used to remind and monitor patients from a variety of sources, such as multiple doctors' offices, and/or multiple hospitals, and/or multiple pharmacy dispensaries, and/or individual patients. Consequently, server 458 is electronic linked to plurality of different patient's electronic devices 456a, 456b, 456c, 456d, 456e; and their associated pill boxes 410a, 410b, 410c, 410d, 410e; and their associated caregivers 460a, 460b, 460c, 460d, and 460d. The linkages are represented by the reference characters "L", "M", "N", "O", and "P" in FIG. 18. The bi-directional arrows indicate that communication occurs in both directions down the pathway, as has been described with reference to FIG. 17. In addition to this system being able to provide the individual service providers (doctors, hospitals, etc.) and individual patients and caregivers with compliance information, the server 458 can also produce reports that will advise a pharmaceutical firm or government agency with compliance information. Additionally, other relevant information such as reported side effects of a particular medication could also be recorded and stored, and ultimately reported, if desired.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of the invention are an example and the invention is not limited to the exact details shown or described.

The invention claimed is:

1. A method of reminding a patient to take a dose of a medication in a timely fashion comprising the steps of:
    providing an electronic pill box having a housing with a plurality of dosettes disposed therein, where each dosette has one or more chambers defined therein and each chamber has a door that is movable between an open and closed position; an illumination device positioned to illuminate an underside of the door of each chamber; and a switch operatively engaged with each illumination device;
    providing a reminder schedule to a microprocessor in the pill box housing;
    loading appropriate chambers corresponding to the reminder schedule of medication with an appropriate dose of a medication;
    tracking real time relative to the reminder schedule;
    providing a first reminder to the patient to take a particular dose of medication from a particular chamber when the real time corresponds to a time on the reminder schedule and wherein the first reminder includes illuminating the door of the particular chamber with a first color light emitted by the associated illumination device;
    issuing a second reminder to the patient if the door to the particular chamber is not opened within a present period of time;
    providing an electronic device accessible to the patient;
    linking the electronic device to the pill box so that bidirectional communication between the electronic device and pill box is possible; and wherein the steps of issuing either of the first and second reminders to the patient further includes providing an alert to the patient via the electronic device; and
    recording a compliance event by responding on the electronic device to the alert provided to the patient.

2. The method as defined in claim 1, further comprising the steps of:
    providing a remote server; and
    electronically linking the remote server to one or both of the electronic
    device and the pill box.

3. The method as defined in claim 2, further comprising the step of:
    entering data relating to the patient and to the reminder schedule into the remote server; and
    controlling the reminder schedule from the remote schedule.

4. The method as defined in claim 3, wherein the step of entering date includes:
    entering data into a dedicated website operatively linked to the server; or
    entering data into a dedicated electronic medical server (EMR) and then syncing the EMR with the server.

5. The method as defined in claim 4, further comprising the step of:
    electronically linking a caregiver's electronic device with the server; and
    contacting the caregiver via their electronic device if the patient fails to take the particular dose after issuance of a second reminder.

6. The method as defined in claim 5, further comprising the steps of:
    linking the server to multiple sets of patients' pill boxes, patients' electronic devices; and caregivers' electronic devices so as to monitor multiple patients simultaneously.

7. The method as defined in claim 1, wherein the step of issuing the second reminder further includes emitting an audible sound from the housing of the pill box.

8. The method as defined in claim 1, wherein the step of linking the electronic device to the pill box includes connecting the electronic device and pill box to each other utilizing WiFi or Bluetooth technology.

9. The method as defined in claim 1, wherein the step of providing the alert to the patient includes sending the patient one or more of a voice message, an email, a text, a Tweet®, a Facebook® post, a push notification or a pager notification.

* * * * *

UNITED STATES PATENT AND TRADEMARK OFFICE
CERTIFICATE OF CORRECTION

PATENT NO. : 9,317,663 B2  
APPLICATION NO. : 13/966037  
DATED : April 19, 2016  
INVENTOR(S) : Robert G. Dickie et al.

Page 1 of 1

It is certified that error appears in the above-identified patent and that said Letters Patent is hereby corrected as shown below:

Claims

Column 21, line 39 (Claim 1) change "present" to --preset--.

Signed and Sealed this
Thirty-first Day of May, 2016

Michelle K. Lee
*Director of the United States Patent and Trademark Office*